United States Patent
Gunaratnam

(10) Patent No.: US 9,248,251 B2
(45) Date of Patent: *Feb. 2, 2016

(54) MASK WITH INTEGRAL CUSHION AND FOREHEAD PIECE

(71) Applicant: ResMed Limited, Bella Vista, New South Wales (AU)

(72) Inventor: Michael Kassipillai Gunaratnam, Sydney (AU)

(73) Assignee: RESMED LIMITED, Bella Vista (AT)

( * ) Notice: Subject to any disclaimer, the term of this patent is extended or adjusted under 35 U.S.C. 154(b) by 0 days.

This patent is subject to a terminal disclaimer.

(21) Appl. No.: 14/321,291

(22) Filed: Jul. 1, 2014

(65) Prior Publication Data

US 2014/0311495 A1    Oct. 23, 2014

Related U.S. Application Data

(60) Continuation of application No. 13/526,711, filed on Jun. 19, 2012, now Pat. No. 8,794,239, which is a continuation of application No. 12/801,883, filed on Jun. 30, 2010, now Pat. No. 8,210,180, which is a (Continued)

(51) Int. Cl.
*A61M 11/00* (2006.01)
*A61M 16/06* (2006.01)
*A61M 16/00* (2006.01)

(52) U.S. Cl.
CPC ....... *A61M 16/0622* (2014.02); *A61M 16/0057* (2013.01); *A61M 16/06* (2013.01); *A61M 16/065* (2014.02); *A61M 16/0616* (2014.02); *A61M 16/0633* (2014.02); *A61M 16/0638* (2014.02); *A61M 16/0683* (2013.01)

(58) Field of Classification Search
USPC ............. 128/205.25, 206.21, 206.12, 206.24, 128/207.11, 207.13, 206.27, 207.17
See application file for complete search history.

(56) References Cited

U.S. PATENT DOCUMENTS

| | | | |
|---|---|---|---|
| 781,516 A | 1/1905 | Guthrie |
| 812,706 A | 2/1906 | Warbasse |
| 1,081,745 A | 12/1913 | Johnston et al. |
| 1,192,186 A | 7/1916 | Greene |

(Continued)

FOREIGN PATENT DOCUMENTS

| | | |
|---|---|---|
| AU | 91/77110 B | 11/1991 |
| AU | 94/64816 B | 12/1994 |

(Continued)

OTHER PUBLICATIONS

Mask 1 Photographs, Respironics Inc., Reusable Full Mask (small) Part #452033 Lot #951108.

(Continued)

*Primary Examiner* — Steven Douglas
(74) *Attorney, Agent, or Firm* — Nixon & Vanderhye, P.C.

(57) ABSTRACT

A respiratory mask has an adjustable forehead support member that is simple and inexpensive to manufacture. The forehead support member may be adjusted by rotating a forehead pad about an off-center bore or by bending an angular adjustment beam. The mask has a mask cushion with an accordionate membrane having at least two hinged portions. The mask may be constructed with a mask frame, the mask cushion, and the forehead support member molded as one piece.

20 Claims, 20 Drawing Sheets

Related U.S. Application Data continuation of application No. 11/957,593, filed on Dec. 17, 2007, now Pat. No. 7,762,259, which is a division of application No. 10/821,204, filed on Apr. 9, 2004, now Pat. No. 7,503,327.

(60) Provisional application No. 60/461,414, filed on Apr. 10, 2003.

(56) References Cited

U.S. PATENT DOCUMENTS

| | | |
|---|---|---|
| 1,653,572 A | 12/1927 | Jackson |
| 1,926,027 A | 9/1933 | Biggs |
| 2,123,353 A | 7/1938 | Catt |
| 2,245,969 A | 6/1941 | Francisco et al. |
| 2,248,477 A | 7/1941 | Lombard |
| 2,254,854 A | 9/1941 | O'Connell |
| 2,317,608 A | 4/1943 | Heidbrink |
| 2,371,965 A | 3/1945 | Lehmberg |
| 2,376,871 A | 5/1945 | Fink |
| 2,415,846 A | 2/1947 | Randall |
| 2,438,058 A | 3/1948 | Kincheloe |
| 2,578,621 A | 12/1951 | Yant |
| 2,590,006 A | 3/1952 | Gordon |
| 2,931,356 A | 4/1960 | Schwarz |
| D188,084 S | 5/1960 | Garelick |
| 2,939,458 A | 6/1960 | Lundquist |
| 3,013,556 A | 12/1961 | Galleher |
| 3,182,659 A | 5/1965 | Blount et al. |
| 3,189,027 A | 6/1965 | Bartlett |
| 3,193,624 A | 7/1965 | Webb et al. |
| 3,238,943 A | 3/1966 | Holley |
| 3,315,674 A | 4/1967 | Bloom et al. |
| 3,330,273 A | 7/1967 | Bennett |
| 3,362,420 A | 1/1968 | Blackburn et al. |
| 3,363,833 A | 1/1968 | Laerdal |
| 3,556,122 A | 1/1971 | Laerdal |
| 3,580,051 A | 5/1971 | Blevins |
| 3,700,000 A | 10/1972 | Hesse et al. |
| 3,720,235 A | 3/1973 | Schrock |
| 3,750,333 A | 8/1973 | Vance |
| 3,752,157 A | 8/1973 | Malmin |
| 3,796,216 A | 3/1974 | Schwarz |
| 3,799,164 A | 3/1974 | Rollins |
| D231,803 S | 6/1974 | Huddy |
| 3,830,230 A | 8/1974 | Chester |
| 4,077,404 A | 3/1978 | Elam |
| D250,131 S | 10/1978 | Lewis et al. |
| 4,120,302 A | 10/1978 | Ziegler |
| 4,167,185 A | 9/1979 | Lewis |
| 4,226,234 A | 10/1980 | Gunderson |
| 4,245,632 A | 1/1981 | Houston |
| D262,322 S | 12/1981 | Mizerak |
| 4,304,229 A | 12/1981 | Curtin |
| 4,328,797 A | 5/1982 | Rollins et al. |
| 4,347,205 A | 8/1982 | Stewart |
| 4,354,488 A | 10/1982 | Bartos |
| 4,402,316 A | 9/1983 | Gadberry |
| 4,412,537 A | 11/1983 | Tiger |
| 4,467,799 A | 8/1984 | Steinberg |
| 4,522,639 A | 6/1985 | Ansite et al. |
| 4,558,710 A | 12/1985 | Eichler |
| D285,496 S | 9/1986 | Berman |
| 4,616,647 A | 10/1986 | McCreadie |
| 4,622,964 A | 11/1986 | Flynn |
| 4,655,213 A | 4/1987 | Rapoport et al. |
| 4,665,570 A | 5/1987 | Davis |
| 4,671,271 A | 6/1987 | Bishop et al. |
| 4,677,975 A | 7/1987 | Edgar et al. |
| 4,677,977 A | 7/1987 | Wilcox |
| H397 H | 1/1988 | Stark |
| D293,613 S | 1/1988 | Wingler |
| 4,739,755 A | 4/1988 | White et al. |
| 4,770,169 A | 9/1988 | Schmoegner et al. |
| 4,774,941 A | 10/1988 | Cook |
| 4,782,832 A | 11/1988 | Trimble et al. |
| 4,799,477 A | 1/1989 | Lewis |
| 4,809,692 A | 3/1989 | Nowacki et al. |
| 4,819,629 A | 4/1989 | Jonson |
| 4,821,713 A | 4/1989 | Bauman |
| 4,841,953 A | 6/1989 | Dodrill |
| 4,848,334 A | 7/1989 | Bellm |
| 4,848,366 A | 7/1989 | Aita et al. |
| 4,907,584 A | 3/1990 | McGinnis |
| 4,910,806 A | 3/1990 | Baker et al. |
| 4,919,128 A | 4/1990 | Kopala et al. |
| 4,938,210 A | 7/1990 | Shene |
| 4,938,212 A | 7/1990 | Snook et al. |
| 4,944,310 A | 7/1990 | Sullivan |
| D310,431 S | 9/1990 | Bellm |
| 4,971,051 A | 11/1990 | Toffolon |
| 4,986,269 A | 1/1991 | Hakkinen |
| 4,989,596 A | 2/1991 | Macris et al. |
| 4,989,599 A | 2/1991 | Carter |
| 5,005,568 A | 4/1991 | Loescher et al. |
| 5,005,571 A | 4/1991 | Dietz |
| 5,027,809 A | 7/1991 | Robinson |
| 5,038,776 A | 8/1991 | Harrison et al. |
| 5,042,473 A | 8/1991 | Lewis |
| 5,042,478 A | 8/1991 | Kopala et al. |
| 5,046,200 A | 9/1991 | Feder |
| 5,063,922 A | 11/1991 | Hakkinen |
| 5,069,205 A | 12/1991 | Urso |
| D323,908 S | 2/1992 | Hollister et al. |
| 5,109,839 A | 5/1992 | Blasdell et al. |
| 5,109,840 A | 5/1992 | Daleiden |
| 5,121,745 A | 6/1992 | Israel |
| 5,133,347 A | 7/1992 | Huennebeck |
| 5,140,980 A | 8/1992 | Haughey et al. |
| 5,140,982 A | 8/1992 | Bauman |
| 5,159,938 A | 11/1992 | Laughlin |
| 5,178,138 A | 1/1993 | Walstrom et al. |
| D334,633 S | 4/1993 | Rudolph |
| 5,220,699 A | 6/1993 | Farris |
| 5,231,983 A | 8/1993 | Matson et al. |
| 5,233,978 A | 8/1993 | Callaway |
| 5,243,971 A | 9/1993 | Sullivan et al. |
| 5,245,995 A | 9/1993 | Sullivan et al. |
| 5,265,595 A | 11/1993 | Rudolph |
| 5,279,289 A | 1/1994 | Kirk |
| 5,280,784 A | 1/1994 | Kohler |
| 5,311,862 A | 5/1994 | Blasdell et al. |
| 5,322,057 A | 6/1994 | Raabe et al. |
| 5,322,059 A | 6/1994 | Walther |
| 5,343,878 A | 9/1994 | Scarberry et al. |
| 5,357,951 A | 10/1994 | Ratner |
| 5,372,130 A | 12/1994 | Stern et al. |
| 5,388,571 A | 2/1995 | Roberts et al. |
| 5,404,871 A | 4/1995 | Goodman et al. |
| 5,419,318 A | 5/1995 | Tayebi |
| 5,429,126 A | 7/1995 | Bracken |
| 5,429,683 A | 7/1995 | Le Mitouard |
| 5,431,158 A | 7/1995 | Tirotta |
| 5,438,981 A | 8/1995 | Starr et al. |
| 5,441,046 A | 8/1995 | Starr et al. |
| D362,061 S | 9/1995 | McGinnis et al. |
| 5,477,852 A | 12/1995 | Landis et al. |
| 5,479,920 A | 1/1996 | Piper et al. |
| 5,481,763 A | 1/1996 | Brostrom et al. |
| 5,488,948 A | 2/1996 | Dubruille et al. |
| 5,492,116 A | 2/1996 | Scarberry et al. |
| 5,501,214 A | 3/1996 | Sabo |
| 5,509,404 A | 4/1996 | Lloyd et al. |
| 5,517,986 A | 5/1996 | Starr et al. |
| 5,538,000 A | 7/1996 | Rudolph |
| 5,540,223 A | 7/1996 | Starr et al. |
| 5,542,128 A | 8/1996 | Lomas |
| 5,546,936 A | 8/1996 | Virag et al. |
| 5,558,090 A | 9/1996 | James |
| RE35,339 E | 10/1996 | Rapoport |
| 5,560,354 A | 10/1996 | Berthon-Jones et al. |
| 5,570,682 A | 11/1996 | Johnson |
| 5,570,689 A | 11/1996 | Starr et al. |
| D377,089 S | 12/1996 | Starr et al. |

(56) References Cited

U.S. PATENT DOCUMENTS

| | | |
|---|---|---|
| 5,592,938 A | 1/1997 | Scarberry et al. |
| 5,608,647 A | 3/1997 | Rubsamen et al. |
| 5,642,730 A | 7/1997 | Baran |
| 5,647,355 A | 7/1997 | Starr et al. |
| 5,647,357 A | 7/1997 | Barnett et al. |
| 5,649,532 A | 7/1997 | Griffiths |
| 5,649,533 A | 7/1997 | Oren |
| 5,655,520 A | 8/1997 | Howe et al. |
| 5,655,527 A | 8/1997 | Scarberry et al. |
| 5,657,493 A | 8/1997 | Ferrero et al. |
| 5,657,752 A | 8/1997 | Landis et al. |
| 5,662,101 A | 9/1997 | Ogden et al. |
| 5,666,946 A | 9/1997 | Langenback |
| 5,685,296 A | 11/1997 | Zdrojkowski et al. |
| 5,687,715 A | 11/1997 | Landis et al. |
| 5,715,814 A | 2/1998 | Ebers |
| 5,724,965 A | 3/1998 | Handke et al. |
| 5,746,201 A | 5/1998 | Kidd |
| 5,813,423 A | 9/1998 | Kirchgeorg |
| 5,832,918 A | 11/1998 | Pantino |
| D402,755 S | 12/1998 | Kwok |
| 5,921,239 A | 7/1999 | McCall et al. |
| 5,937,851 A | 8/1999 | Serowski et al. |
| 6,016,804 A | 1/2000 | Gleason et al. |
| D423,096 S | 4/2000 | Kwok |
| 6,044,844 A | 4/2000 | Kwok et al. |
| D428,987 S | 8/2000 | Kwok |
| 6,098,205 A | 8/2000 | Schwartz et al. |
| 6,112,746 A | 9/2000 | Kwok et al. |
| 6,119,693 A | 9/2000 | Kwok |
| 6,123,071 A | 9/2000 | Berthon-Jones et al. |
| 6,152,137 A | 11/2000 | Schwartz et al. |
| D439,326 S | 3/2001 | Hecker et al. |
| D443,355 S | 6/2001 | Gunaratnam et al. |
| 6,257,237 B1 | 7/2001 | Suzuki |
| 6,341,606 B1 | 1/2002 | Bordewick et al. |
| 6,374,826 B1 | 4/2002 | Gunaratnam et al. |
| 6,397,847 B1 | 6/2002 | Scarberry et al. |
| 6,463,931 B1 | 10/2002 | Kwok et al. |
| 6,467,483 B1 | 10/2002 | Kopacko et al. |
| D468,823 S | 1/2003 | Smart |
| 6,520,182 B1 | 2/2003 | Gunaratnam |
| 6,532,961 B1 | 3/2003 | Kwok et al. |
| 6,557,556 B2 | 5/2003 | Kwok |
| 6,595,214 B1 | 7/2003 | Hecker |
| D484,237 S | 12/2003 | Lang et al. |
| 6,679,261 B2 | 1/2004 | Lithgow |
| 6,691,707 B1 | 2/2004 | Gunaratnam et al. |
| 6,691,708 B2 | 2/2004 | Kwok et al. |
| D492,992 S | 7/2004 | Guney et al. |
| 6,926,004 B2 | 8/2005 | Schumacher |
| 7,100,610 B2 | 9/2006 | Biener et al. |
| 7,503,327 B2 | 3/2009 | Gunaratnam |
| 7,762,259 B2 | 7/2010 | Gunaratnam |
| 2003/0019496 A1 | 1/2003 | Kopacko et al. |
| 2003/0034034 A1 | 2/2003 | Kwok et al. |
| 2003/0062048 A1 | 4/2003 | Gradon |
| 2003/0089373 A1 | 5/2003 | Gradon |
| 2003/0221691 A1 | 12/2003 | Biener et al. |
| 2004/0045550 A1 | 3/2004 | Lang et al. |
| 2004/0045551 A1 | 3/2004 | Eaton |
| 2004/0177850 A1 | 9/2004 | Gradon |
| 2006/0260614 A1 | 11/2006 | Biener et al. |
| 2008/0092899 A1 | 4/2008 | Gunaratnam |
| 2011/0000491 A1 | 1/2011 | Gunaratnam |
| 2012/0247476 A1 | 10/2012 | Gunaratnam |

FOREIGN PATENT DOCUMENTS

| | | |
|---|---|---|
| AU | 95/16178 B | 7/1995 |
| AU | 32914/95 | 2/1996 |
| AU | 9459430 | 2/1996 |
| AU | A 41018/97 | 4/1998 |
| AU | A 89312/98 | 1/1999 |
| CA | 1039144 | 9/1928 |
| DE | 459104 | 4/1928 |
| DE | 701 690 | 1/1941 |
| DE | 159396 | 6/1981 |
| DE | 3015279 A1 | 10/1981 |
| DE | 3345067 A1 | 6/1984 |
| DE | 3537507 | 4/1987 |
| DE | 3539073 A1 | 5/1987 |
| DE | 4004157 C1 | 4/1991 |
| DE | 4343205 A1 | 6/1995 |
| DE | 29715718 | 10/1997 |
| DE | 197 35 359 | 1/1998 |
| DE | 29723101 U1 | 7/1998 |
| DE | 298 10846 U1 | 8/1998 |
| DE | 198 17 332 A1 | 1/1999 |
| DE | 198 08 105 A1 | 9/1999 |
| DE | 20005346 | 5/2000 |
| DE | 29923141 U | 5/2000 |
| DE | 199 54 517 A1 | 6/2001 |
| DE | 10045183 | 5/2002 |
| EP | 0 054 154 | 10/1981 |
| EP | 0 252 052 A1 | 1/1988 |
| EP | 0 264 772 A1 | 4/1988 |
| EP | 0 386 605 A1 | 2/1990 |
| EP | 0 427 474 A2 | 5/1991 |
| EP | 0 462 701 A1 | 12/1991 |
| EP | 0 602 424 | 11/1993 |
| EP | 0 608 684 A1 | 8/1994 |
| EP | 0 697 225 | 7/1995 |
| EP | 0 178 925 A2 | 4/1996 |
| EP | 0 747 078 A2 | 12/1996 |
| EP | 0 821 978 | 2/1998 |
| EP | 1099452 | 5/2001 |
| EP | 1205205 | 11/2001 |
| FR | 2 574 657 A1 | 6/1986 |
| FR | 2 658 725 A1 | 8/1991 |
| FR | 2 749 176 | 12/1997 |
| GB | 1395391 | 5/1975 |
| GB | 1 467 828 | 3/1977 |
| GB | 2145335 A | 3/1985 |
| GB | 2147506 A | 5/1985 |
| GB | 2 164 569 A | 3/1986 |
| GB | 2 186 801 | 8/1987 |
| GB | 2 267 648 A | 12/1993 |
| JP | 09/216240 A | 8/1997 |
| JP | 11-000397 | 1/1999 |
| WO | WO 80/01044 | 5/1980 |
| WO | WO 82/03548 | 10/1982 |
| WO | WO 86/06969 | 12/1986 |
| WO | WO 87/01950 | 4/1987 |
| WO | WO 91/03277 | 3/1991 |
| WO | WO 92/15353 | 9/1992 |
| WO | WO 92/20395 | 11/1992 |
| WO | WO 93/01854 | 2/1993 |
| WO | WO 94/02190 | 2/1994 |
| WO | WO 94/16759 | 8/1994 |
| WO | WO 94/20051 | 9/1994 |
| WO | WO 95/02428 | 1/1995 |
| WO | WO 96/17643 | 6/1996 |
| WO | WO 96/25983 | 8/1996 |
| WO | WO 96/39206 | 12/1996 |
| WO | WO 97/07847 | 3/1997 |
| WO | WO 97/41911 | 11/1997 |
| WO | WO 98/04310 | 2/1998 |
| WO | WO 98/11930 | 3/1998 |
| WO | WO 98/12965 | 4/1998 |
| WO | WO 98/18514 | 5/1998 |
| WO | WO 98/24499 | 6/1998 |
| WO | WO 98/26829 | 6/1998 |
| WO | WO 98/26830 | 6/1998 |
| WO | WO 98/34665 | 8/1998 |
| WO | WO 98/48878 | 11/1998 |
| WO | WO 99/43375 | 9/1999 |
| WO | WO 99/58181 | 11/1999 |
| WO | WO 00/57942 | 10/2000 |
| WO | WO 00/78381 | 12/2000 |
| WO | WO 00/78384 A1 | 12/2000 |
| WO | WO 01/97892 | 12/2001 |
| WO | WO 03/059427 | 7/2003 |

(56) References Cited

FOREIGN PATENT DOCUMENTS

| WO | WO 2004/022144 | 3/2004 |
|---|---|---|
| WO | WO 2004/022145 | 3/2004 |
| WO | WO 2004/078228 | 9/2004 |

OTHER PUBLICATIONS

Mask 2 Photographs, Puritan—Bennett, Adam Curcuit, Shell Part #231700, Swivel Part #616329-00, Pillows (medium) Part #616324.
Mask 3 Photographs, DeVilbiss Healthcare Inc., Devilbiss Seal-Ring and CPAP Mask Kit (medium), Part #73510-669.
Mask 4 Photographs, Respironics Inc., Monarch Mini Mask with Pressure Port, Part #572004, Monarch Headgear, Part #572011.
Mask 5 Photographs, Healthdyne Technologies, Nasal CPAP Mask (medium narrow), Part #702510.
Mask 6 Photographs, Healthdyne Technologies, Soft Series Nasal CPAP Mask, Part #702020.
Mask 7 Photographs, DeVilbiss Healthcare Inc., Small Mask and Seal Rings, Part #73510-668.
Mask 8 Photographs, Respironics Inc., Reusable Contour Mask (medium), Part #302180.
Mask 9 Photographs, Healthdyne Technologies, Healthdyne Large Headgear.
Mask 10 Photographs, Respironcs Inc., Soft Cap (medium), Part #302142.
Mask 11 Photographs, Weinmann: Hamburg, Nasalmaskensystem mit Schalldämpfer (medium), Part #WN 23105.
Mask 12 Photographs, Life Care.
Mask 13 Photographs, Healthdyne Technologies.
Mask 14 Photographs, King System.
Mask 15 Photographs, Respironics Inc., Pediatric Mask.
Mask 16 Photographs, Hans Rudolph Inc., Hans Rudolph Silicon Rubber Face Mask/8900.
Photograph of Weinmann Mask, acquired prior to 1998.
The ResMed Range of Mask Systems, product brochure, Nov. 1995, 4 pages.
Product Brochure for ResMed "Sullivan® Mirage™—The Mirage is Real. A Perfect Fit—First Time," © 1997 ResMed Limited, 4 pages.
Product Brochure for ResMed "Sullivan® Mirage™—The Mirage is Real. A Perfect Fit—First Time," © 1998 ResMed Limited, 4 pages.
Somnotron CPAP-Gerat WM 2300 instruction manual, Weinmann Hamburg, 11 pages, 1991.
9 Photographs of Weinmann mask, WM 23122, 1999.
ResMed Ltd., "Improving partient compliance with the ResMed Range of Mask Systems the Ultimate Interface for CPAP treatment," 4 pages.

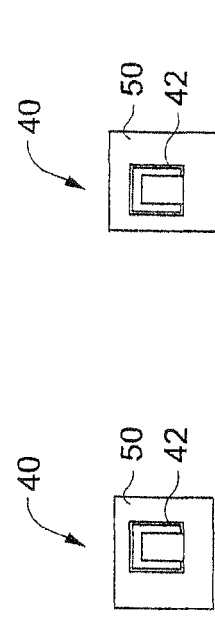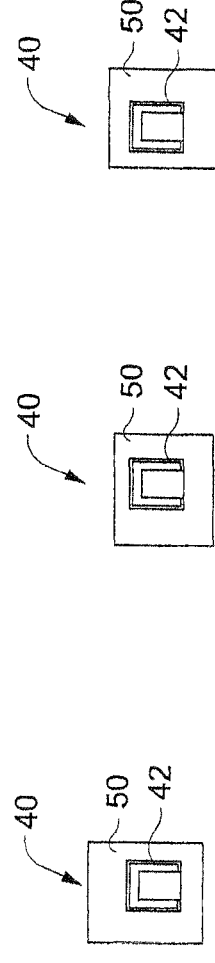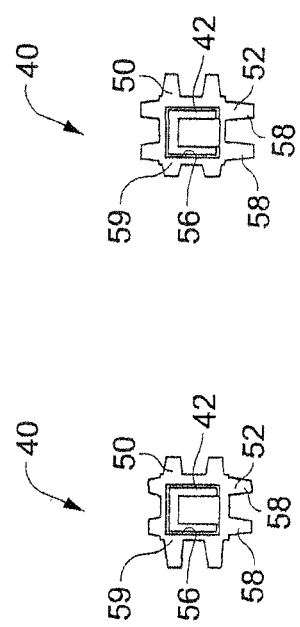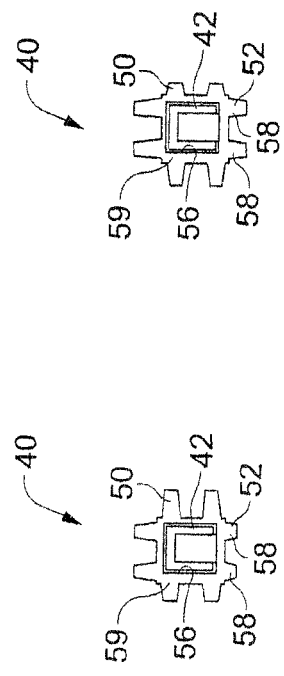
Fig. 13a Fig. 13b Fig. 13c Fig. 13d
Fig. 14a Fig. 14b Fig. 14c Fig. 14d

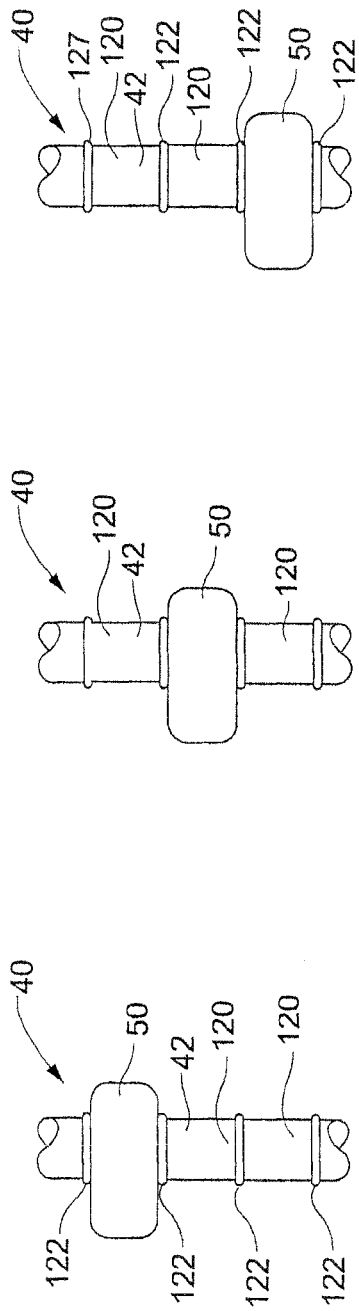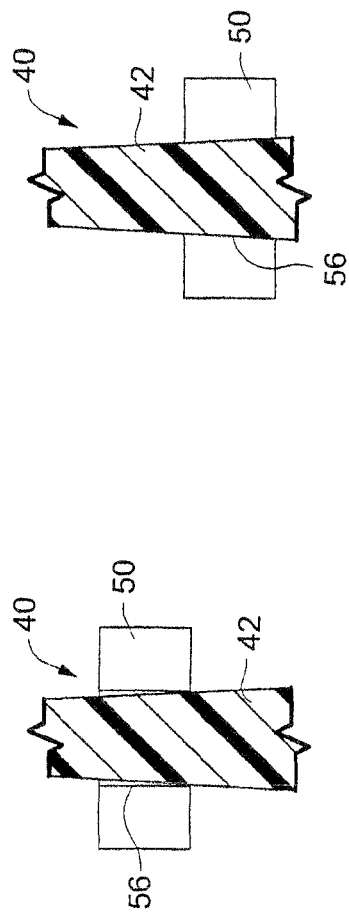

MASK WITH INTEGRAL CUSHION AND FOREHEAD PIECE

CROSS-REFERENCE TO RELATED APPLICATIONS

This application is a continuation of Ser. No. 13/526,711, filed Jun. 19, 2012, which is a continuation of U.S. patent application Ser. No. 12/801,883, filed Jun. 30, 2010, now U.S. Pat. No. 8,210,180, which is a continuation of U.S. Ser. No. 11/957,593, filed Dec. 17, 2007, now U.S. Pat. No. 7,762,259, which is a divisional of U.S. Ser. No. 10/821,204, filed Apr. 9, 2004, now U.S. Pat. No. 7,503,327, which claims the benefit of U.S. Provisional Application Ser. No. 60/461,414, filed Apr. 10, 2003, each incorporated herein by reference in its entirety.

FIELD OF THE INVENTION

The present invention relates to a facial mask with an integral cushion and forehead piece used to supply breathable gas to a wearer's airways.

The invention has been developed primarily for use in supporting a nasal mask used in Continuous Positive Airway Pressure (CPAP) treatment of, for example, Obstructive Sleep Apnea (OSA) and other ventilation assistance treatments such as Non-Invasive Positive Pressure Ventilation (NIPPV) and will be described hereinafter with reference to this application. However, it will be appreciated that the invention is not limited to these particular uses.

BACKGROUND OF THE INVENTION

CPAP treatment is a common ameliorative treatment for breathing disorders including OSA. CPAP treatment, as described in U.S. Pat. No. 4,944,310, provides pressurized air or other breathable gas to the entrance of a patient's airways at a pressure elevated above atmospheric pressure, typically in the range of 4-20 cm $H_2O$. It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders that can involve a relatively higher pressure of gas being provided in the patient mask during the inspiratory phase of respiration and a relatively lower pressure or atmospheric pressure being provided in the patient mask during the expiratory phase of respiration. In other NIPPV modes, the pressure can be made to vary in a complex manner throughout the respiratory cycle. For example, the pressure at the mask during inspiration or expiration can be varied through the period of treatment.

Typically, the ventilation assistance for CPAP or NIPPY treatment is delivered to the patient by way of a nasal mask. Alternatively, a mouth mask full-face mask or nasal prongs can be used.

In this specification, any reference to CPAP treatment is to be understood as embracing all of the above-described forms of ventilation treatment or assistance.

A CPAP apparatus broadly includes a flow generator for supplying a continuous source of pressurized air or other breathable gas. Such a flow generator is typically a stand-alone unit having an electric motor driving a blower and is typically controlled by a servo-controller under the control of a microcontroller unit. Alternatively, other supplies of pressurized gas can be used. The flow generator is connected to the mask by a gas supply conduit or tube to supply the pressurized gas to an interior of the mask. The mask or gas supply conduit generally includes a venting system to vent exhalation gases from the interior of the mask to the atmosphere. The mask is normally secured to the wearer's head by a headgear or straps. The straps are adjusted with sufficient tension to achieve a gas-tight seal between the mask and the wearer's face. The mask generally includes a forehead support to rest against the user's forehead to support and stabilize the mask with respect to the user's face and prevent the mask from exerting undue pressure on the user's nose when the straps are tensioned. Examples of nasal masks are shown in U.S. Pat. Nos. 4,782,832 and 5,243,971.

One problem that arises with the use of masks is that a single shape of mask must be utilized for a large variety of users having differently shaped and sized heads and facial regions. Therefore, it is desirable for the forehead support to be adjustable to alter an extension between a forehead contacting portion of the forehead support and the mask frame, thereby accommodating a variety of users with a single mask configuration, while maintaining a comfortable fit and gas-tight seal for each user. Additionally, an adjustable forehead support can be adjusted to position the gas supply conduit in a desired position with respect to the user, such as to prevent the gas supply conduit from contacting the wearer's forehead or face and causing discomfort to the user.

Adjustable forehead supports are known. See, for example, the adjustable forehead supports disclosed in U.S. Pat. No. 6,119,693 to Kwok et al. and PCT International Patent Application Publication No. WO 00/78384 to Kwok et al., both assigned to the assignee of the present application. Both references disclose effective, durable forehead support mechanisms. However, these mechanisms require several components that increase the expense of manufacturing such mechanisms and make the mechanisms more appropriate for masks that will be used over an extended period of time, generally 3-6 months. Such mechanisms are relatively costly to use with masks intended for single or short-term use.

There are circumstances where an inexpensive, disposable short-term use mask is appropriate. For instance, such a mask might be appropriate under CPAP testing conditions where the testing is expected to last only a few days or weeks. Such a mask might also be used for patients admitted to hospitals for short-term stays. Extended use masks require periodic disassembly, cleaning and disinfecting, and reassembly to maintain sanitary conditions. The use of a disposable mask can eliminate such mask maintenance during extended treatment. Instead of performing the mask maintenance at the periodic intervals, a user can just dispose the disposable mask at the proper intervals and use a new disposable mask. However, for it to be generally desirable to use a disposable mask in such extended term treatment, the cost of the mask must be sufficiently low so as to compare favorably economically with the overall cost of an extended use mask, including the cost of the extended use mask, as well as the time required and nuisance of the periodic maintenance of the extended use mask.

Thus, there is a need for an inexpensive short-term use mask for providing breathable gases to a patient, as during CPAP treatment. To accommodate a large variety of users comfortably with a single mask configuration and maintain a gas-tight seal for each user, the mask should include a simple, easy to use adjustable forehead support mechanism. The mask should be inexpensive enough to be disposable during extended term CPAP treatment while comparing favorably economically to the use of an extended term mask. The mask should also be inexpensive enough to justify single-use. It is an object of the present invention to provide such a mask.

SUMMARY OF THE INVENTION

The present invention addresses the above needs by providing a respiratory mask with an adjustable forehead support that is constructed with few moving parts, and with as many parts as possible molded as one piece or co-molded together in a single process. The present invention provides a mask that is not only low in cost, but also is easy to adjust due to the simplicity of the adjustable forehead support.

A respiratory mask is provided having a mask frame, a mask cushion attached to the frame and a forehead support member integrally formed with the mask frame. A plurality of strap attachment portions are provided on the mask frame for attaching straps to the respiratory mask to secure the respiratory mask to a head and facial region of a user. The forehead support includes a forehead pad having a bore mounted over a forehead support member. The support pad bore has a number of sides, and the outer surface of the forehead support member has a cross-section with a corresponding number of sides, such that the support pad can be mounted over the forehead support member in a number of distinct angular positions corresponding to the number of sides of the support pad bore. An exterior surface of the support pad has a number of sides corresponding to the number of sides of the support pad bore, each exterior side preferably having a different spacing to an axis of the forehead support member than the other sides. In this manner, a number of different extensions between a forehead-contacting portion of the support pad and the mask frame can be provided by changing the angular position of the support pad with respect to the forehead support member.

An alternative embodiment of the mask includes a mask frame, molded in a flat configuration, having a cushion supporting portion, an air inlet portion and a forehead support portion. A mask cushion is attached to the mask frame cushion supporting portion. The forehead support portion and mask frame air inlet members are connected to the mask frame cushion supporting portion by hinges such that the air inlet portion can be folded over the cushion supporting portion and the forehead support portion can be folded over the air inlet portion with a cooperative locking mechanism on the mask frame interlocking the components in a final folded configuration ready for wearing. The forehead support portion includes a pair of forehead support adjustment mechanisms adjustable as to height to adjust the extension of a forehead support pad relative to the interlocked mask frame and mask cushion. The mask frame also includes portions for attaching to headgear or straps to secure the mask to the head and facial region of the user.

A method of manufacturing a respiratory mask is provided including molding integrally in a generally flat configuration, a mask frame having a cushion supporting portion, an air inlet portion and a forehead support portion, with the forehead support portion and mask frame air inlet members being connected to the mask frame cushion supporting portion by hinges such that the air inlet portion can be folded over the cushion supporting portion and the forehead support portion can be folded over the air inlet portion and locked in a final wearable configuration. A mask cushion is also molded to or otherwise attached to the mask frame cushion supporting portion.

BRIEF DESCRIPTION OF THE DRAWINGS

Preferred embodiments of the invention will now be described, by way of examples only, with reference to the accompanying drawings in which:

FIGS. 13a-d are partial schematic top plan views of an alternative embodiment of a forehead support of the present invention;

FIGS. 14a-d are partial schematic top plan views of an alternative embodiment of a forehead pad of the present invention;

FIGS. 15a-c are partial elevational views of an alternative embodiment of the forehead support of the present invention;

FIGS. 16a and 16b are partial side elevational schematic views of an alternative embodiment of the forehead support of the present invention;

FIGS. 20a-e show bottom perspective detail views corresponding to FIGS. 19a-c;

DETAILED DESCRIPTION OF PREFERRED EMBODIMENTS

In the included figures a nasal mask is depicted, but the current invention is not intended to be limited to nasal masks. The aspects of the current invention are equally applicable to a mouth or full-face mask.

Figure 1:
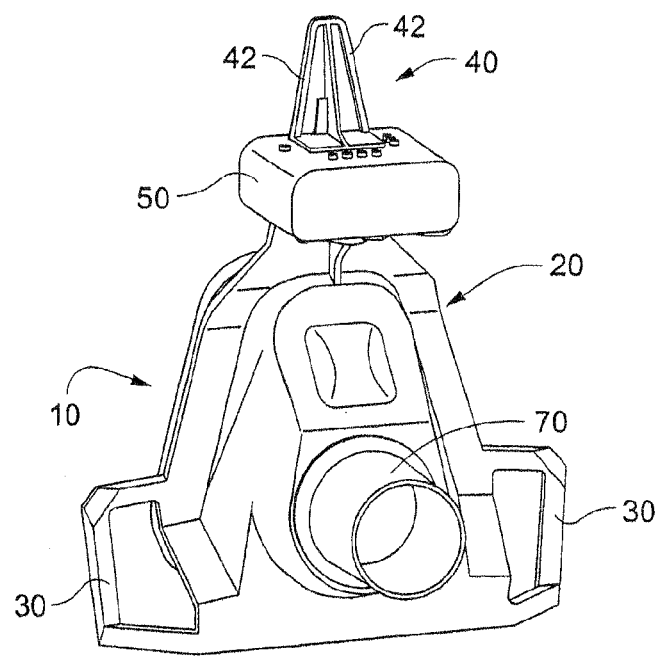
FIG. 1 is a front perspective view of a first embodiment of a mask according to the invention.
Figure 2:
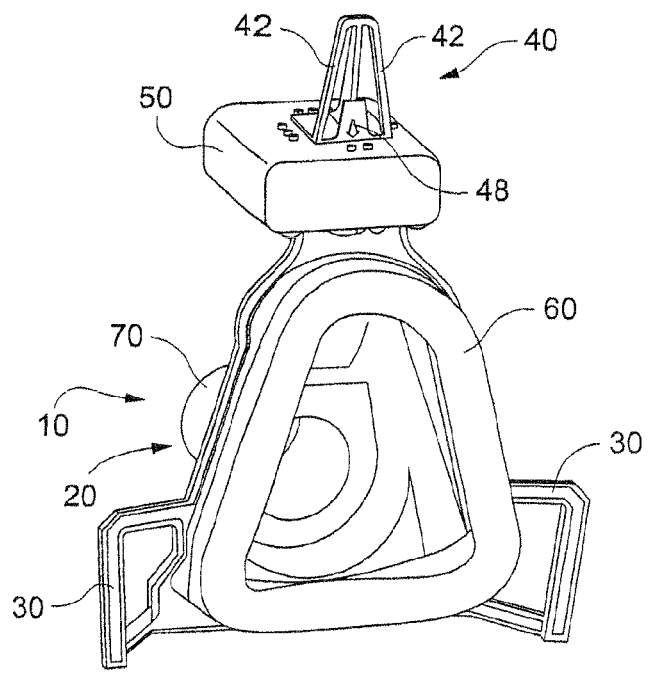
FIG. 2 is a rear perspective view of the mask shown in FIG. 1.

FIGS. 1 and 2 show front and rear perspective views of an embodiment of the present invention. A nasal mask 10 has a mask frame 20, strap attachment portions 30, a forehead support 40 including a forehead support member 42 and a forehead pad 50, and a mask cushion 60. The mask also has a single air inlet tube 70 mounted on the mask frame 20 for supplying pressurized gas to an interior of the mask 10. Pressurized gas is supplied to the mask 10 by an air supply conduit (not shown) connected between the air inlet tube 70 and a pressurized air supply (not shown). As is known, an exhaust vent can be provided on the mask 10 or air supply conduit for exhausting exhalation gases from an interior of the mask. Other embodiments may have vents, elbows, pressure ports, or other attachments for items such as a sense tube or oxygen supply port as further options. There may also be further attachment portions for straps or other types of headgear.

Figure 3A:
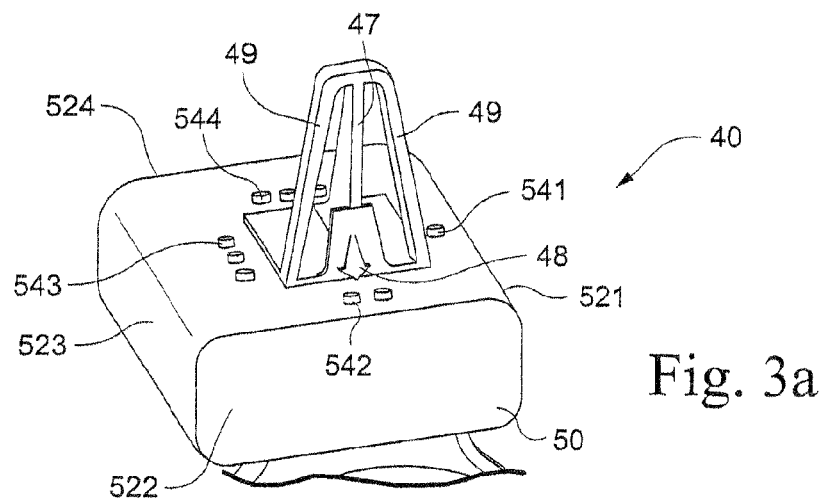
FIG. 3a is an enlarged perspective view of the forehead support of the mask according to the first embodiment of the invention.
Figure 3B:
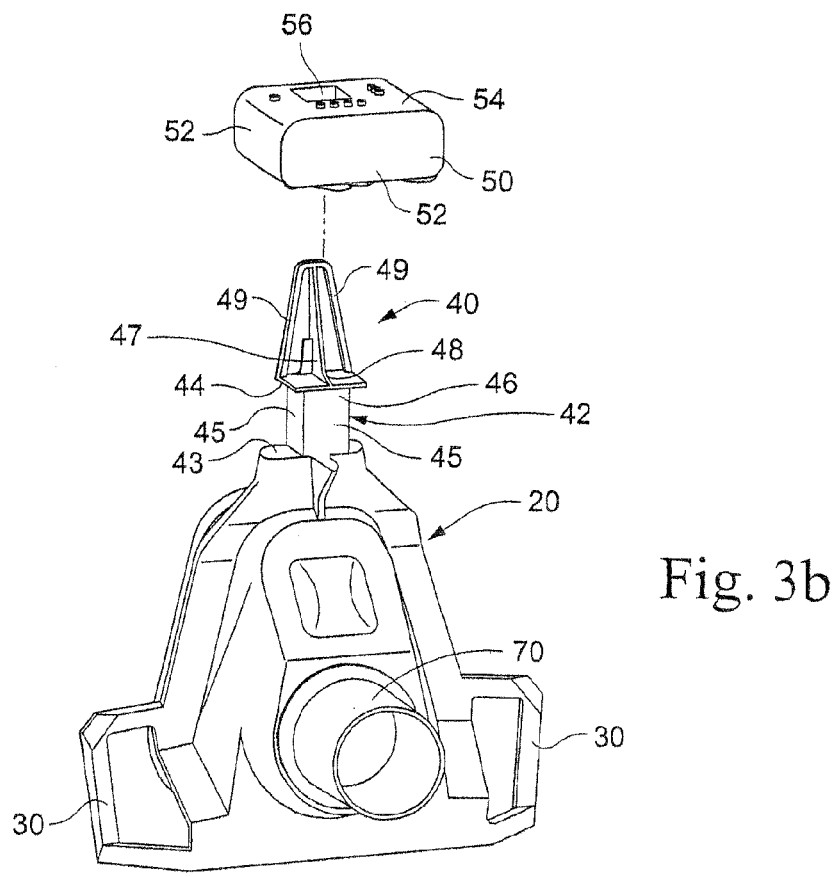
FIG. 3b is an exploded view of the forehead support of the mask according to the first embodiment of the invention.

FIG. 3*a* is an enlarged perspective view of the forehead pad 50 and FIG. 3*b* is an exploded view of the mask frame 20, forehead support member 42 and the forehead pad 50. In this embodiment, forehead support member 42, is attached to and extends upwardly from mask frame 20. Forehead support member 42 includes a lower supporting surface 43, an upper supporting surface 44 and an upright column 46 positioned between the supporting surfaces 43 and 44 having four exterior sides 45. Two upper strap attachment portions 49 are mounted on opposing sides of an upper portion of the forehead support member 42 and are reinforced by brace member 47 attached to and extending between an upper portion of the upper strap attachment portions 49 and the upper portion of the forehead support member 42. A position indicating marker 48 is attached to the brace member 47. In the preferred embodiment, upright column 46 is solid to add strength to the forehead support member 42. In alternative embodiments, the upright column 46 can be hollow or can have a strengthening insert molded therein.

In this embodiment, the forehead pad 50 is an elastomeric pad, having four exterior sides 52, denoted individually as sides 521, 522, 523 and 524, and an off-center bore 56. The off-center square bore 56 is defined by four inner surfaces 561, 562, 563, and 564, corresponding to sides 521, 522, 523 and 524, respectively. The bore 56 is configured and sized so as to be able to mount over the upright column 46 in a mating fashion. Upper supporting surface 44 and lower supporting surface 43 are sized to be somewhat larger than the size of bore 56 so that when the forehead pad is mounted over the forehead support member 42, the upper and lower supporting surfaces will retain the forehead pad in place on the forehead support member 42. The elasticity of the forehead pad 50 allows the forehead pad 50 to pass over the larger upper supporting surface 44 when installing or removing the forehead pad 50 with respect to the forehead support member 42.

Figure 3C:
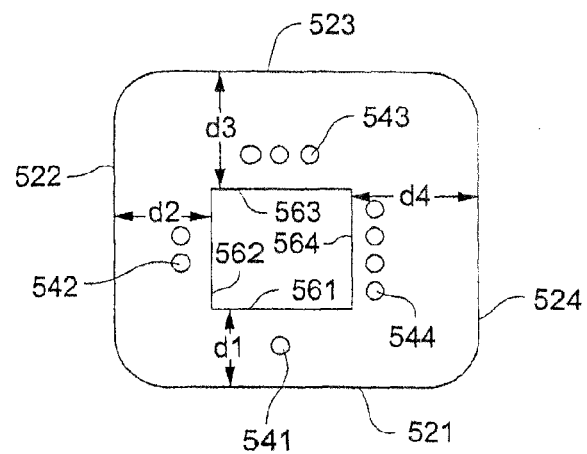
FIG. 3c is a top plan view of the forehead pad of the mask according to the first embodiment of the invention.

Since the bore 56 is off-center, a distance between an axis of the bore 56 and the exterior sides 52 is different for each side 521, 522, 523, and 524, which in the embodiment shown, increases from side 521 to side 522 to side 523 to side 524. See FIG. 3*c*, which shows a distance d4 for side 524 greater than a distance d3 for side 523 greater than a distance d2 for side 522 greater than a distance d1 for side 521. In this embodiment, the forehead pad can be mounted on the forehead support member in four different angular positions. In each angular position, a different side 52 will be facing toward the user to contact the user's forehead. Since the distance between each side 52 and the axis of the bore 56 is different, changing the angular position of the forehead pad 50 with respect to the forehead support member will alter the distance between the forehead support member 42 and the user's forehead, allowing the forehead support 40 to be adjusted as desired for each user.

Each exterior side 52 has a corresponding position indicator 54, denoted individually as position indicators 541, 542, 543 and 544, corresponding to sides 521, 522, 523 and 524, respectively. These position indicators 54 are depicted as rounded projections, which provide a visual and tactile indicator of the position of the forehead pad 50 when mounted on the forehead support member. As shown, position indicator 541 includes one raised projection, position indicator 542 includes two raised projections, position indicator 543 includes three raised projections and position indicator 544 includes four raised projections. Alternatively, the position indicators can be in the form of printed markings, notches, labels or other forms of visual and/or tactile indicators. The user is able to determine which angular position the forehead pad is in by determining which position indicator 54 is aligned with the position indicating marker 48.

The bore 56 need not be of continuous cross-section, and need not extend from one end of the forehead pad 50 to the other, but rather may be open at only one end. Its configuration may also be tapered or have other provisions in order to effectively lock the forehead pad 50 to the mask 10 so that it will resist moving from the chosen position when in use. Such locking effect may include the provision of stepped configuration along the forehead support member 42 or the bore 56 such that there is engagement and interference between the two components. Alternative mechanisms for locking the adjusted forehead pad 50 to the forehead support member 42 can also be used.

Figure 4A:
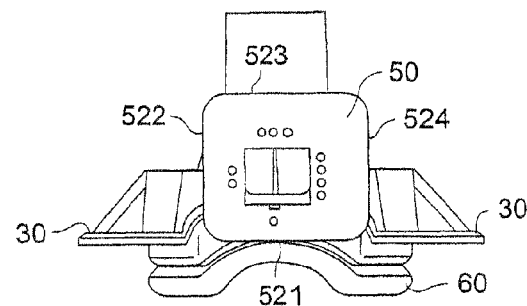
FIGS. 4a-d are top plan views of the forehead support according to the first embodiment in each of four adjustable positions.
Figure 4B:
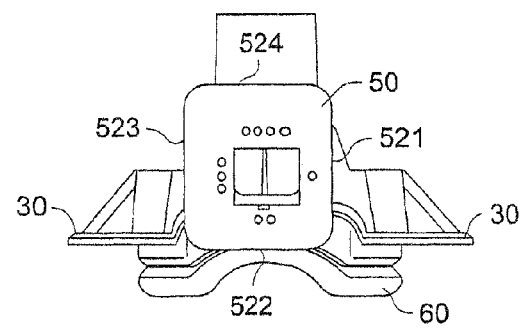
Figure 4C:
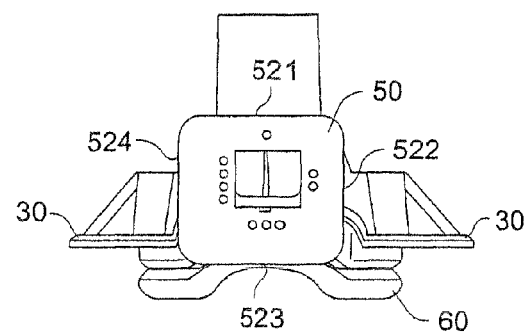
Figure 4D:
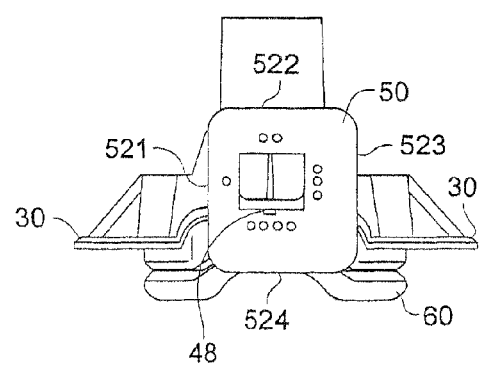
Figure 5D:
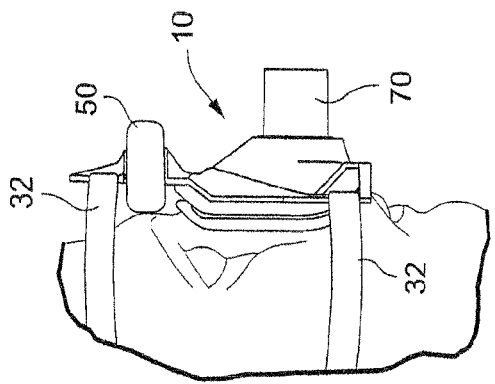
FIGS. 5a-d are side elevational views of the forehead support according to the first embodiment in each of the four adjustable positions on a user's forehead.
Figure 5C:
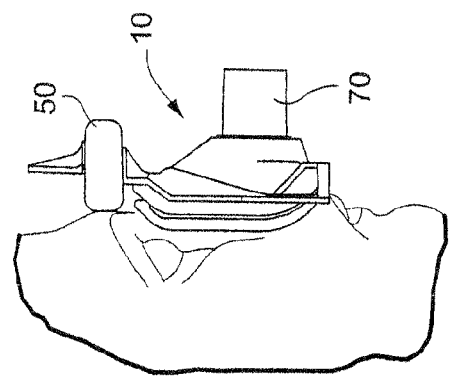
Figure 5B:
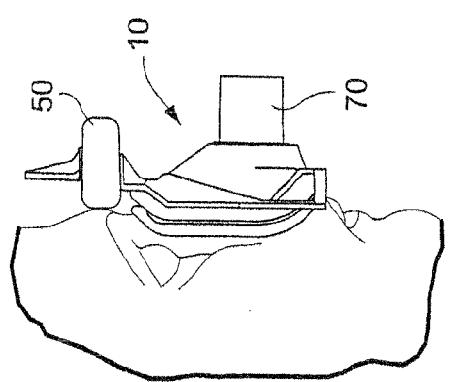
Figure 5A:
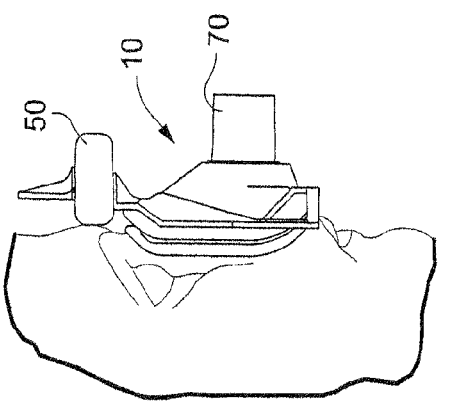

FIGS. 4*a, b, c*, and *d* are top plan view of the mask 10 and FIGS. 5*a, b, c* and *d* are side elevational views of the mask 10 positioned on a user, respectively illustrating the four angular positions of the forehead pad according to this embodiment of the invention. FIGS. 4*a* and 5*a* illustrate the first angular position, appropriate for a user having a protuberant forehead. The forehead pad 50 has been rotated counterclockwise from the first position to the second position illustrated in FIGS. 4*b* and 5*b*. This position is appropriate for a less protuberant forehead than in position 1. The forehead pad 50 has been further rotated counterclockwise from the second position to the third position illustrated in FIGS. 4*c* and 5*c*. This position is appropriate for a slightly receding forehead. Finally, the forehead pad has been rotated counterclockwise from the third position to the fourth position illustrated in FIGS. 4*d* and 5*d*. This position is appropriate for users having a more receding forehead than illustrated in FIG. 5*c*. Although only four positions are shown, fewer or greater than four positions can be provided by suitably altering the number of sides 45, 52 and 56, with a distance between each side 52 and an axis of the forehead support member 42 being different.

Figure 6:
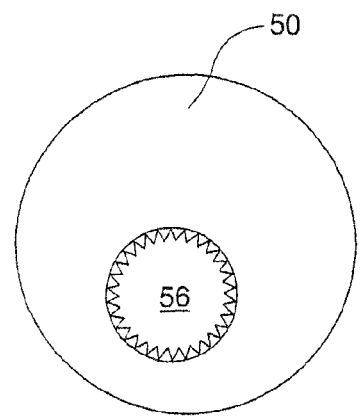
FIG. 6 is a top plan view of an alternative embodiment of the forehead pad.

In an alternative embodiment shown in FIG. 6, the forehead pad 50 can be cam-shaped and have a toothed off-center bore 56 adapted to engage a similarly toothed forehead support member 42 to provide a greater resolution of adjustment, Alternatively, if pad 50 is retained to support 42 by press fit, a generally continuously variable adjustability of the distance from the forehead contacting surface of the pad 50 to the mask frame 20.

Figure 7:
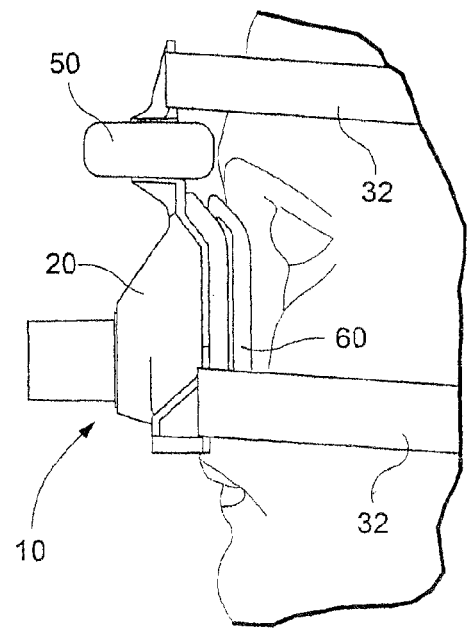
FIG. 7 is a side elevational view of the mask according to the first embodiment secured to a user.

FIG. 7 illustrates a nasal mask 10 of the present invention being worn by a user. Mounting straps 32 are attached to the strap attachment portions 30, to attach the nasal mask to the user's head. The forehead pad 50 contacts the forehead. The mask cushion 60 seals the mask frame 20 to the facial region of the user. The mask cushion 60 is shaped to substantially conform to the facial region of the user. However, the shape of the facial regions of different users varies and the adjustable position of the forehead pad 50 may not be optimal for all users. Therefore, it is desirable for the mask cushion 60 to be flexible and resilient to seal the mask frame 20 to the facial regions of a variety of users.

Figure 8C:
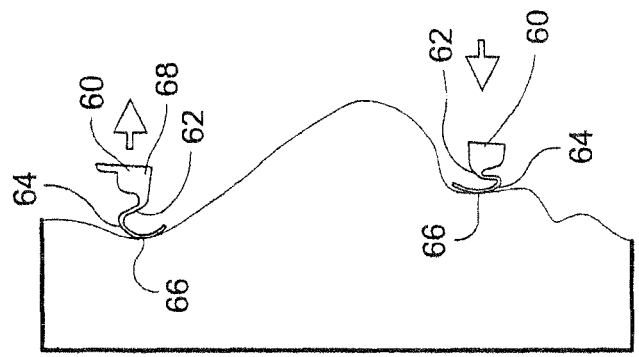
FIGS. 8a-c are schematic drawings depicting the interaction between the cushion and a user's facial region.
Figure 8B:
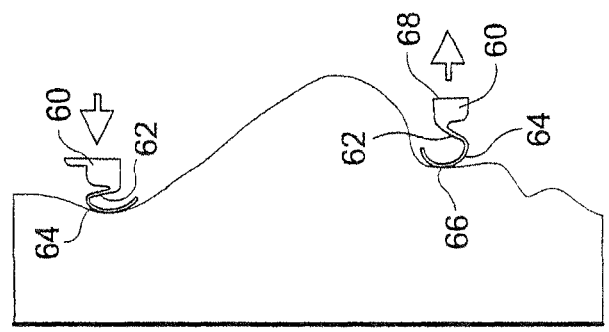
Figure 8A:
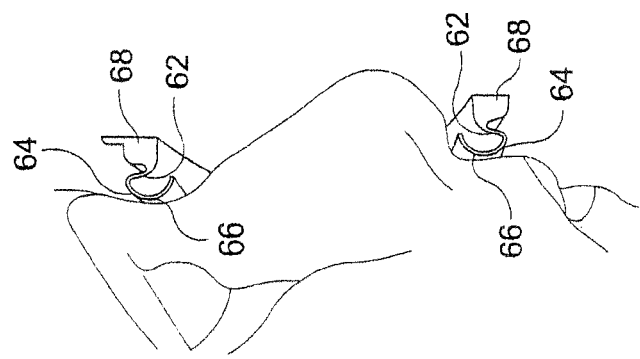

FIGS. 8a, 8b and 8c are schematic diagrams depicting the accordionate configuration and behavior of the mask cushion 60. Cushion 60 includes a face contacting portion 66 connected to a main body 68 of the cushion 60 by cushion hinged portions 62 and 64. If a portion of the mask frame 20 is close to the facial region of the user, the included angles of the two hinged portions 62, 64 will decrease, allowing the face contacting portion 66 to draw closer to the mask frame without causing discomfort to the user. If a portion of the mask frame 20 is not close to the facial region of the user, the included angles of the two hinged portions 62, 64 will increase, allowing the face contacting portion 66 to extend from the mask frame while continuing to maintain a seal with the facial region of the user. FIG. 8a depicts a condition in which the angle between the mask frame 20 and the facial region of the user is substantially optimized. FIG. 8b depicts a condition in which the upper portion of the mask frame 20 is closer to the facial region of the user than the lower portion, and the upper portion of the face contacting portion 66 of the cushion is closer to the cushion main body 68 than the lower portion of the face contacting portion 66 to accommodate for this. FIG. 8c depicts a condition opposite to the condition in FIG. 8b in which the lower portion of the mask frame 20 is closer to the facial region of the user than the upper portion, and the lower portion of the face contacting portion 66 of the cushion is closer to the cushion main body 68 than the upper portion of the face contacting portion 66 to accommodate for this.

Figure 9:
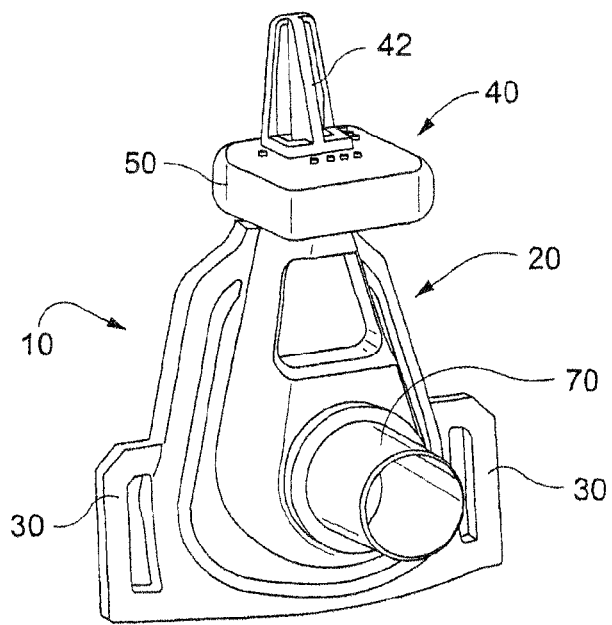
FIG. 9 is a front perspective view of an alternative embodiment of a mask according to the invention.
Figure 10:
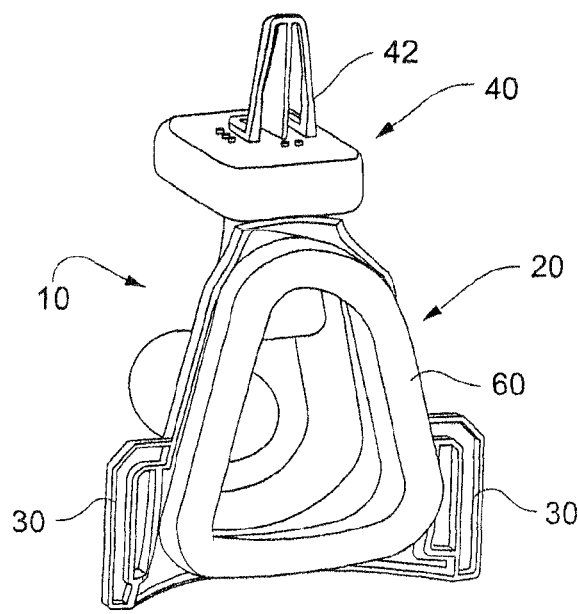
FIG. 10 is a rear perspective view of the mask shown in FIG. 9.

FIGS. 9 and 10 show front and rear perspective views of an alternative embodiment of the present invention. The nasal mask 10 of this embodiment is similar to the embodiment shown in FIGS. 1 and 2 but has a mask frame 20 having a slightly different shape and configuration to improve moldability of the frame, as well as to improve the aesthetic appearance of the frame. This embodiment also has strap attachment portions 30, a forehead support 40 including a forehead support member 42 and a forehead pad 50, a mask cushion 60 and a single air inlet tube 70 mounted on the mask frame 20 for supplying pressurized gas to an interior of the mask 10.

Figure 11:
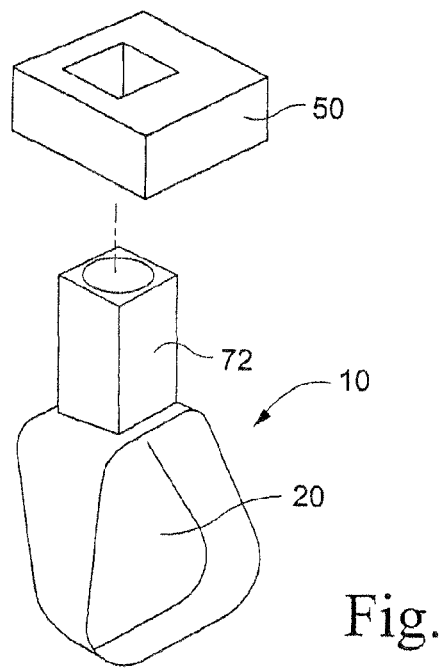
FIG. 11 is a rear perspective schematic view of an alternative embodiment of the present invention.

FIG. 11 is a rear perspective schematic view of an alternative embodiment of the present invention. In the nasal mask 10 of this embodiment, an air inlet tube 72 is mounted to the top of the mask frame 20 and has a square outer cross-section so as to act as the forehead support member 42 of the previous embodiments. As with the previous embodiments, the forehead pad 50 can be placed over the air inlet tube in a plurality of different angular positions to alter a distance between the air inlet tube/forehead support member 72 and allow the mask to be adjusted for each user.

Figure 12:
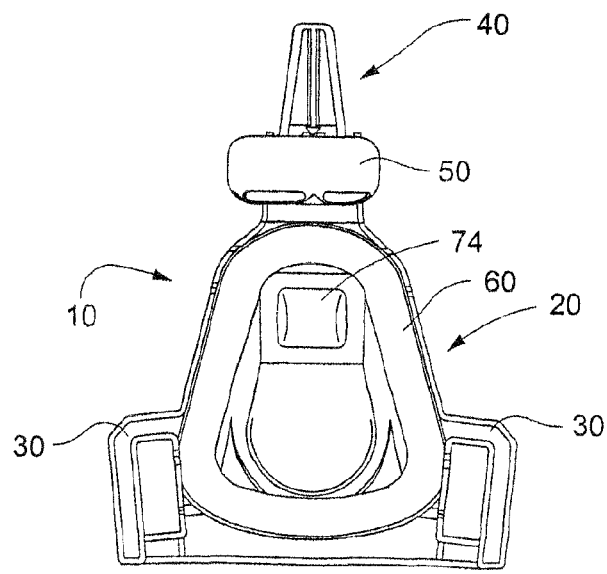
FIG. 12 is a rear elevational view of an alternative embodiment of the present invention.

FIG. 12 is a rear elevational view of an alternative embodiment of the present invention.

FIGS. 13a-d are partial schematic top plan views of an alternative embodiment of the forehead support 40. In this embodiment, the forehead support member 42 is configured to have a U-shaped cross-section. An open end of the U-shaped cross-section is shown as facing toward the user but can be oriented away from the user as well. The U-shape can reduce material required for the forehead support member 42 while retaining the necessary strength. FIGS. 13a-d show the different angular positions of the forehead pad 50 corresponding respectively to the positions shown in FIGS. 4a-d and 5a-d.

FIGS. 14a-d are partial schematic top plan views of an alternative embodiment of the forehead pad 50 positioned on the forehead support member 42 of the embodiment shown in FIGS. 13a-d. The forehead pad 50 of this embodiment is not shaped as a rectangle with flat exterior sides. Rather, each exterior side 52 of the forehead pad is generally U-shaped in cross-section with the open end facing outward. Although the bore 56 is positioned generally in a center of a central portion 59 of the forehead pad 50, the two legs 58 of the U-shaped cross-section of each exterior side 52 have a different height. Because of this configuration, the adjustment of the forehead support 40 can be altered as described above by changing the angular orientation of the forehead pad 50 on the forehead support member 42. FIGS. 14a-d show the different angular positions of the forehead pad 50 corresponding respectively to the positions shown in FIGS. 4a-d, 5a-d and 5a-d. This configuration of forehead pad 50 can reduce the amount of material required to make the pad and can also minimize an area of contact of the forehead pad 50 with the user to increase the comfort of the user.

FIGS. 15a-e are partial elevational views of an alternative embodiment of the forehead support 40. In this embodiment, the forehead support member 42 (or air inlet tube 72) has an extended height to provide for a plurality of different elevational positions for the forehead pad 50. In the embodiment shown, the forehead support member 42 includes three separate elevational adjustment positions 120 bounded on each side by position retaining flanges 122. The forehead pad can be moved to any one of the elevational adjustment positions 120 to provide a desired elevational position of the forehead pad 50 on the nasal mask 10 with respect to the user. The position retaining flanges 122 are larger than the bore 56 in the forehead pad 50 to prevent the forehead pad 50 from moving undesirably up and down the forehead support member 42 once it has been adjusted but due to the flexibility of the forehead pad 50, it can be moved over a position retaining flange 122 by applying sufficient force to the forehead pad 50. The force required to move the forehead pad to a different elevational adjustment position can be altered by altering the size of the position retaining flanges 122 with respect to the bore 56 and/or by changing the flexibility of the forehead pad 50. Three elevational positions of the forehead pad 50 are shown respectively in FIGS. 15a, 15b and 15e. The number of elevational adjustment positions 120 can be altered as desired. In a modified version of this embodiment, retaining flanges can be positioned on the forehead pad 50 to engage grooves or other structure on the forehead support member 42.

FIGS. 16a and 16b are partial side elevational schematic views of an alternative embodiment of the forehead support 40. In this embodiment, the forehead support member 42 is tapered along its length. Because the forehead pad 50 is flexible, it can be moved to a desired position along the forehead support member and the forehead support member will correspondingly expand the bore 56 of the flexible forehead pad 50, creating a friction fit between the forehead pad 50 and the forehead support member 42 that will retain the forehead pad 50 in the adjusted position. FIG. 16a shows the forehead pad 50 in an elevated position with respect to the forehead support member 42 where there is a minimal friction fit and FIG. 16b shows the forehead pad 50 in a lowered position with respect to the forehead support member 42 where there is an increased frictional fit. Thus, this embodiment allows infinite elevational positioning of the forehead pad 50 along a given range of the forehead support member 42, as opposed to the discrete positioning provided by the embodiment of FIGS. 15a-c. The magnitude of retaining force of the friction fit between the forehead pad 50 and the forehead support member 42 can be altered by altering the size and shape of the bore 56, the flexibility, material or surface finish of the forehead pad 50, or the taper, size, shape, material or surface finish of the forehead member 42. In one embodiment, a retaining flange can be provided at a bottom portion of the forehead support member 42 to provide a positive bottom stop to the elevational adjustment of the forehead pad 50.

Figure 17:
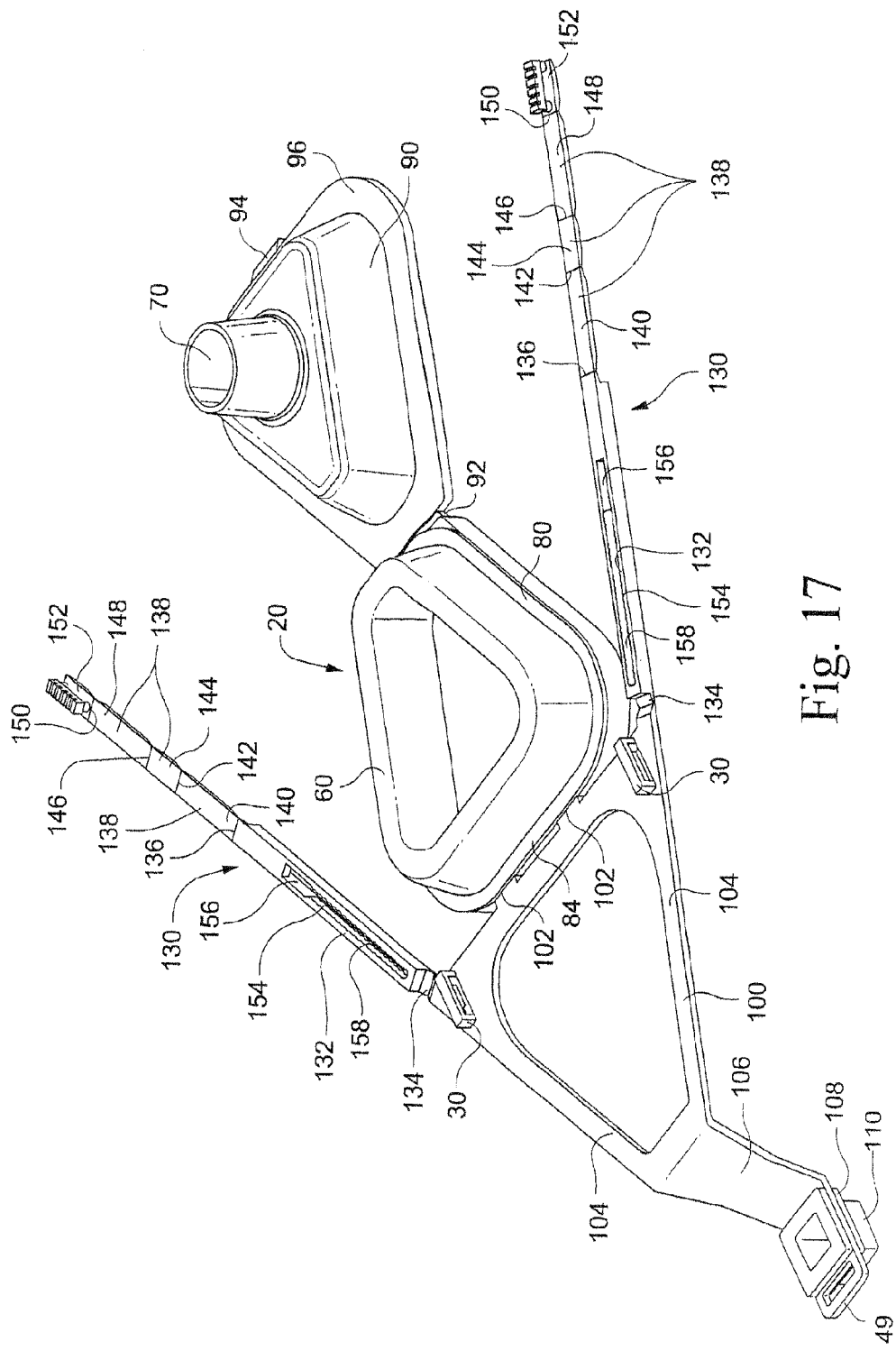
FIG. 17 is a front perspective view of another embodiment of the invention, in a flat, unfolded state, wherein the respiratory mask is molded as a single piece in a generally flat configuration to be folded together for assembly.
Figure 17A:
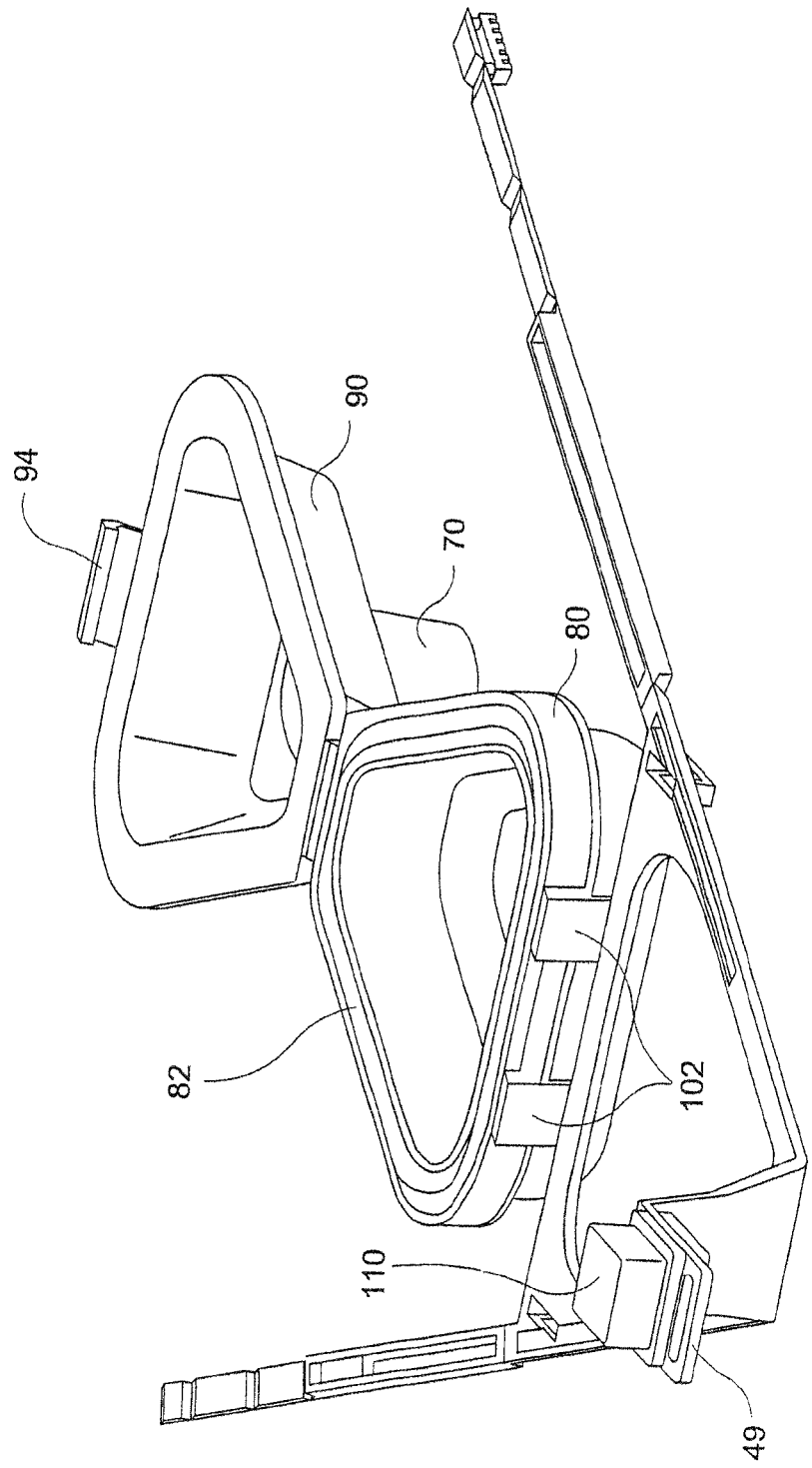
FIG. 17a is a rear perspective view of the embodiment configuration of FIG. 17.
Figure 18:
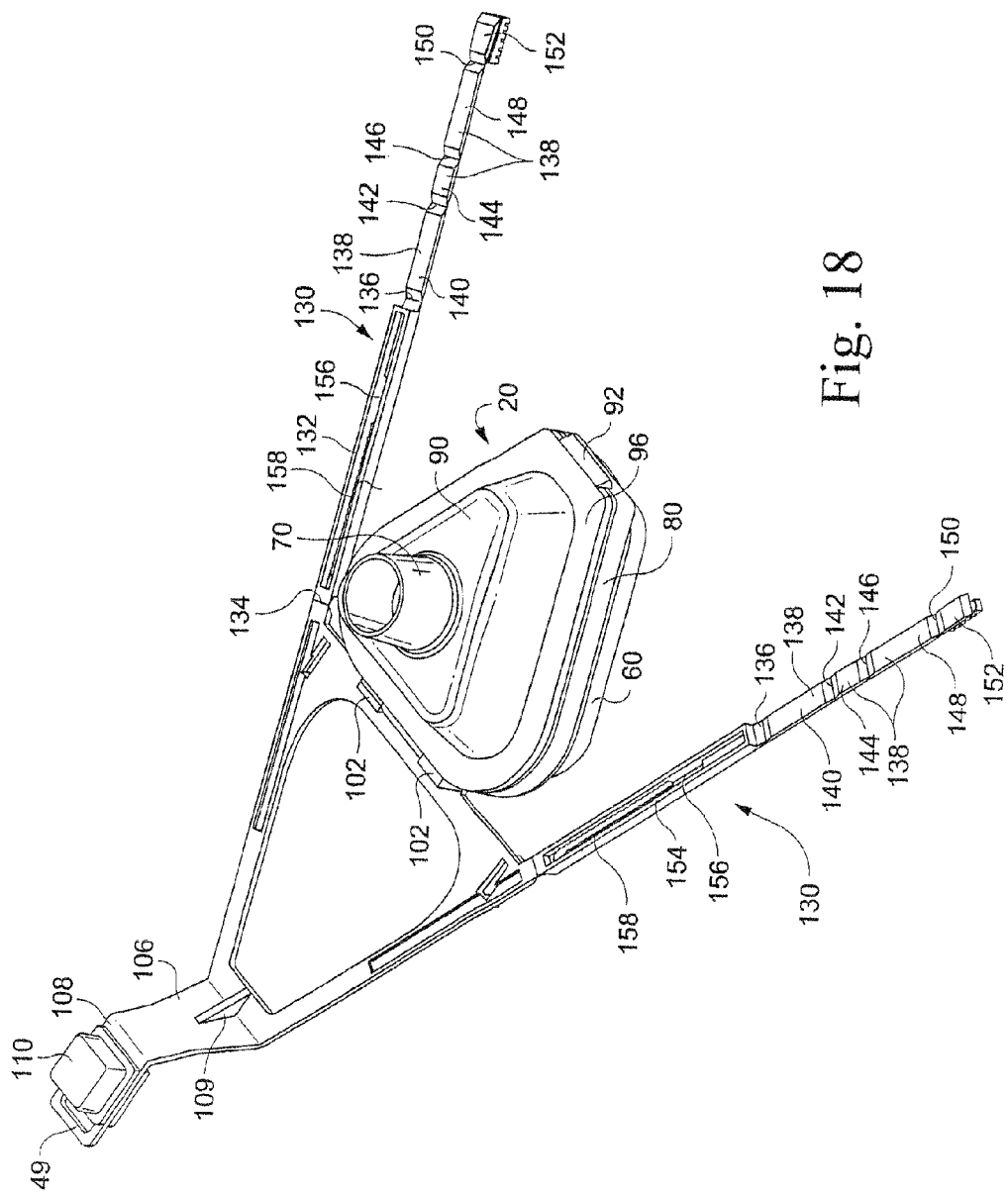
FIG. 18 is a rear perspective view of the embodiment of FIG. 17 wherein the air inlet portion has been folded onto the cushion supporting portion.

FIGS. 17-24 illustrate another embodiment of the invention. In this embodiment, the respiratory mask is molded as a single piece in a generally flat configuration and folded together for assembly. FIG. 17 is a front perspective view of the mask frame in the flat, unfolded state. The mask frame 20 includes a cushion supporting portion 80, an air inlet portion 90 and a forehead support portion 100. An integral hinge 92, also called a "living hinge", is molded between the cushion supporting portion 80 and the air inlet portion 90. An integral hinge 102 is molded between the cushion supporting portion 80 and the forehead support portion 102. In this manner, both the air inlet portion 90 and the forehead support portion 102 can be folded with respect to the cushion supporting portion 80. A sealing member 82 (see FIG. 17a) is provided around a periphery of the cushion supporting member 80 and adapted to sealingly engage the air inlet portion 90 such that when the air inlet portion 90 is folded over onto the cushion supporting portion 80, a gas-tight seal is formed between those two portions to seal an interior of the mask 10. A latch mechanism 94 is attached to a distal edge of the air inlet portion 90 and is adapted to engage a lip 84 on the cushion supporting portion when the two components are folded together to latch the two components in the folded position. See FIG. 18, which is a rear perspective view of the mask 10 wherein the air inlet portion 90 has been folded onto the cushion supporting portion 80 and latched in place.

The forehead support portion 100 has a main body portion 104 and a forehead pad mounting portion 108 interconnected by an offset portion 106 to offset the forehead pad 110 with respect to the main body portion 104. The degree of offset, if any, can be altered as desired for the specific application. Rib 109 between the main body portion 104 and the offset portion 106 adds strength to the forehead support portion 100.

The forehead support portion 100 can utilize the forehead support mechanism 40 discussed above, as shown in FIGS. 25-27 and discussed in more detail below. Alternatively, a nonadjustable forehead pad 110 can be attached to the forehead support portion 100 using methods described herein or molded integrally therewith. In such an embodiment, it is desirable to provide an alternative mechanism for adjusting the forehead pad with respect to the mask frame 20. In one such embodiment, the forehead support portion 100 is provided with a pair of forehead support adjustment mechanisms 130. Each forehead support adjustment mechanism 130 is preferably molded integrally with the forehead support portion 100, although this is not required, and includes an elongated adjustment channel member 132 attached at one end to the forehead support portion 100 by hinge 134. A foldable adjustable height member 138 is attached at another end of the adjustment channel member 132 by hinge 136. The adjustable height member 138 preferably, though not necessarily, includes a side segment 140, top segment 144 and side segment 148 connected together by hinges 142 and 146, respectively, so as to be foldable with respect to one another. See FIGS. 17-18. Alternatively, top member 144 and hinge 146 can be omitted so that side segment 140 is directly connected to side segment 148 by hinge 142. See FIGS. 19-24. An adjustment tab 152 is connected to side member 148 by hinge 150 and is configured and arranged for adjustable engagement with adjustment channel member 132. See FIGS. 19a-c, which show top perspective detail views of the forehead support adjustment mechanism 130 with progressive stages of positioning of the forehead support adjustment mechanism 130, and 20a-c, which show corresponding bottom perspective detail views thereof.

Each elongated adjustment channel member 132 includes a channel 154 including a tab insertion portion 156 and an adjustment portion 158. The adjustment portion 158 of channel 154 includes a pair of sets of uniformly spaced opposed detent slots 160 extending from side walls of the channel 154 inward toward one another. The adjustment tab 152 includes a top retaining portion 162 connected to an adjustment fixing portion 164 connected to a bottom retaining portion 166. See FIGS. 19 and 20. The bottom retaining portion 166 can be grooved (see FIGS. 19a and 20b), ridged or otherwise textured, as can top retaining portion 162 to increase a user's grip on the adjustment tab 152 during adjustment. The adjustment fixing portion 164 includes a pair of sets of outwardly facing detent lugs 168 spaced, configured and dimensioned so as to be able to uniformly engage the detent slots 160 of channel 154 in a temporarily fixed adjustment position until sufficient force is applied to move the detent lugs 168 with respect to the detent slots 160.

Figure 19A:
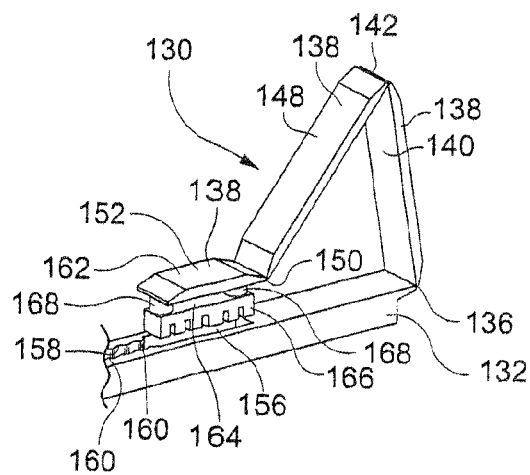
FIGS. 19a-c show top perspective detail views of a forehead support adjustment mechanism of the embodiment of FIG. 17 with progressive stages of positioning of the forehead support adjustment mechanism.
Figure 19B:
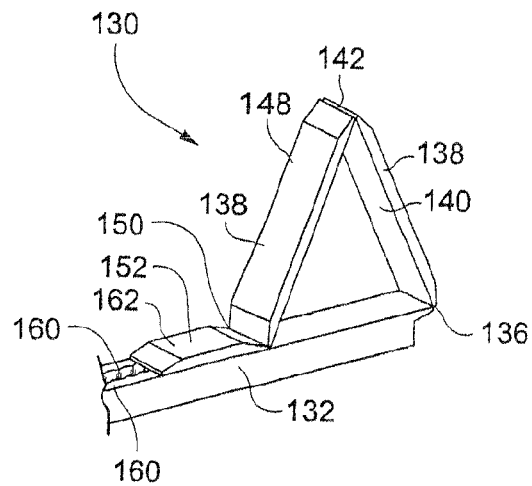
Figure 19C:
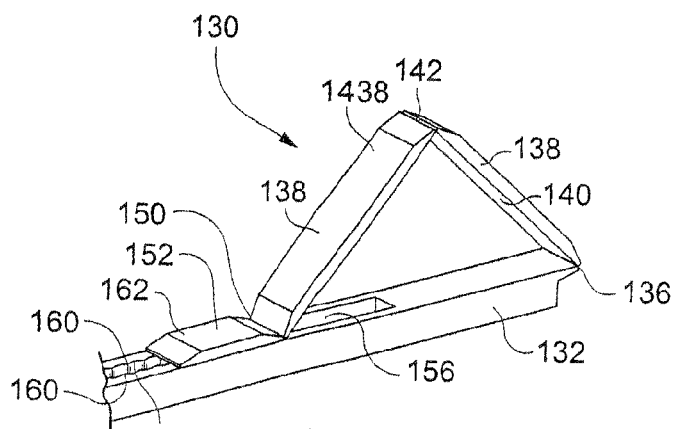
Figure 20A:
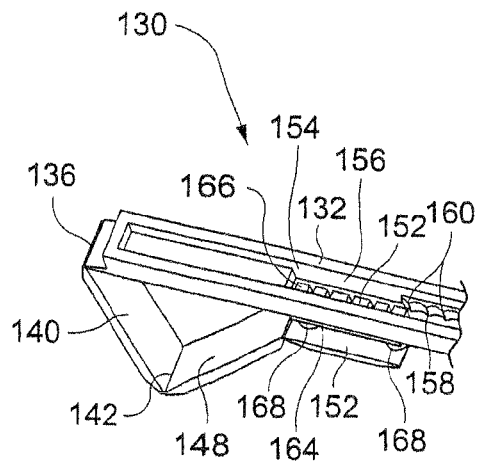
Figure 20B:
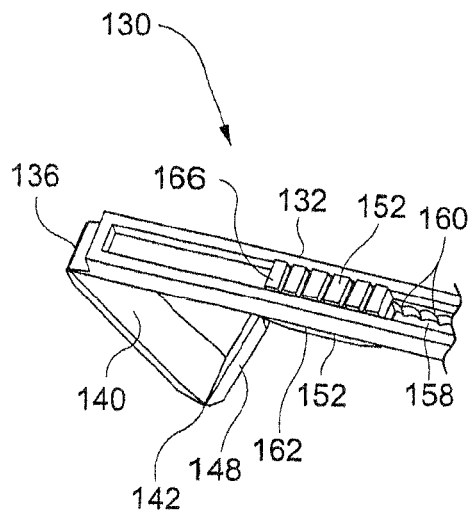
Figure 20C:
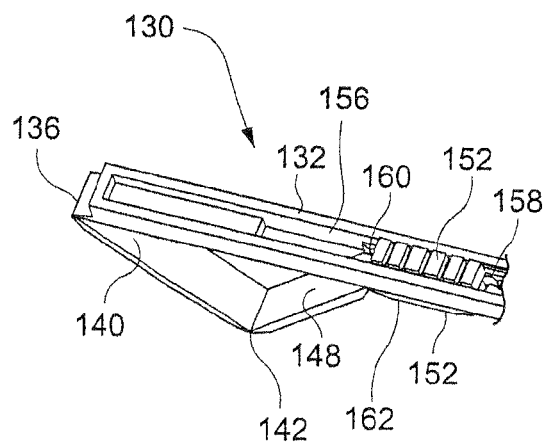
Figure 21:
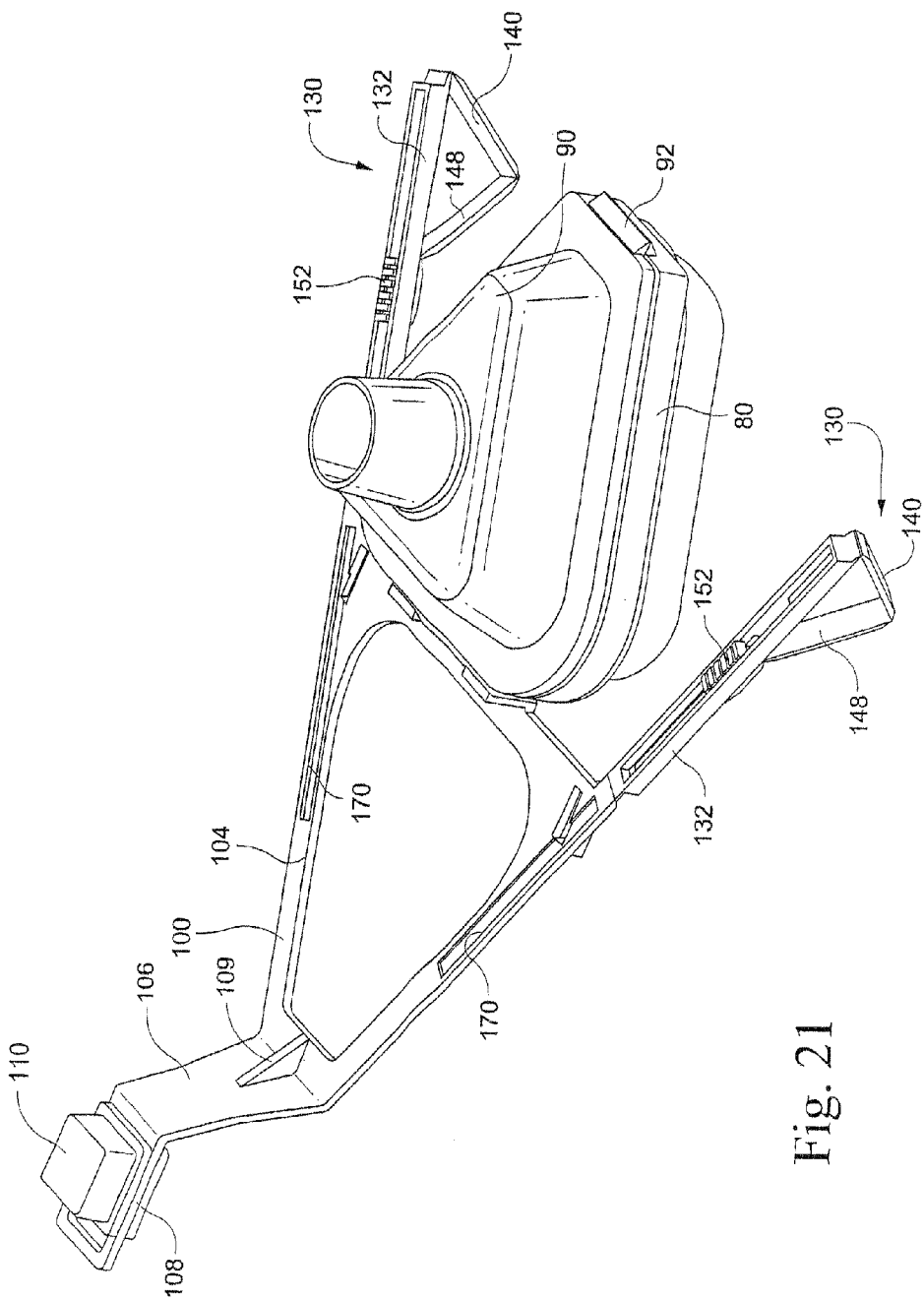
FIG. 21 is a rear perspective view of the embodiment of FIG. 17 with the forehead support adjustment mechanisms assembled.

In a preferred embodiment, a width of the bottom retaining portion 166 of the adjustment tab 152 is less than or equal to a width of the tab insertion portion 156 of the channel 154 and a width of the top retaining portion 162 of the adjustment tab 152 is greater than a width of the tab insertion portion 156 of the channel 154 so as to permit insertion of the adjustment tab 152 into the tab insertion portion 156 (see FIGS. 19a and 20a) until the top retaining portion 162 of the adjustment tab 152 contacts the adjustment channel member 132 to prevent further insertion (see FIGS. 19b and 20b). On the other hand, the width of the bottom retaining portion 166 of the adjustment tab is greater than a minimum width between the opposing sets of detent slots 160 of channel 154 so that when the adjustment tab 152 is moved along the length of the channel 154 from out of the tab insertion portion 156 into the adjustment portion 158 (see FIGS. 19c and 20c), the detent slots 160 engage the bottom retaining portion 166 of adjustment tab 152 to retain adjustment tab 152 in the channel 154 until the adjustment tab 152 is again moved lengthwise along the channel 154 back into the tab insertion portion 156 (see FIGS. 19b and 20b). Adjusting the position of the adjustment tab 152 along the length of the channel 154 allows the overall height of the adjustable height member 138 to be altered with respect to the adjustment channel member 132 and thus, the forehead support portion 100 of the mask, to adjust the height of the forehead support pad, as will be discussed below in further detail. FIG. 21 is a rear perspective view of the mask of this embodiment, with the adjustment tabs 152 positioned in the adjustment portions 158 of the channels 154, respectively.

A minimum inner width between the closest portions of opposed sets of the detent slots 160 of the channel 154 is somewhat smaller than a maximum exterior width of opposed sets of the detent lugs 168 of the adjustment tab 152 so that engagement between the detent slots 160 of channel 154 and the detent lugs 168 of the adjustment tab 152 will temporarily fix the adjustment tab 152 in a desired lengthwise position in the adjustment portion 158 of the channel 154 until sufficient force is applied to overcome such engagement. The force required is determined by a trade-off between balancing the minimum force required to maintain the adjustment tab 152 in a desired adjusted position in the channel 154 when the mask is being worn by the user with the maximum force desired to allow the user the change the adjustment of the adjustment tab 152. These forces can be altered by altering the magnitude of the engagement between opposing detent slots/detent lugs of the channel 154 and adjustment tab 152, respectively, by altering dimensions of the respective detent slot/detent lugs and altering the number and/or shape of the respective detent slots/detent lugs, as well as by altering the material and/or rigidity of the respective detent slots/detent lugs. The positioning of the detent slots and detent lugs on the respective components can be reversed and alternative detent configurations can be used.

Figure 22:
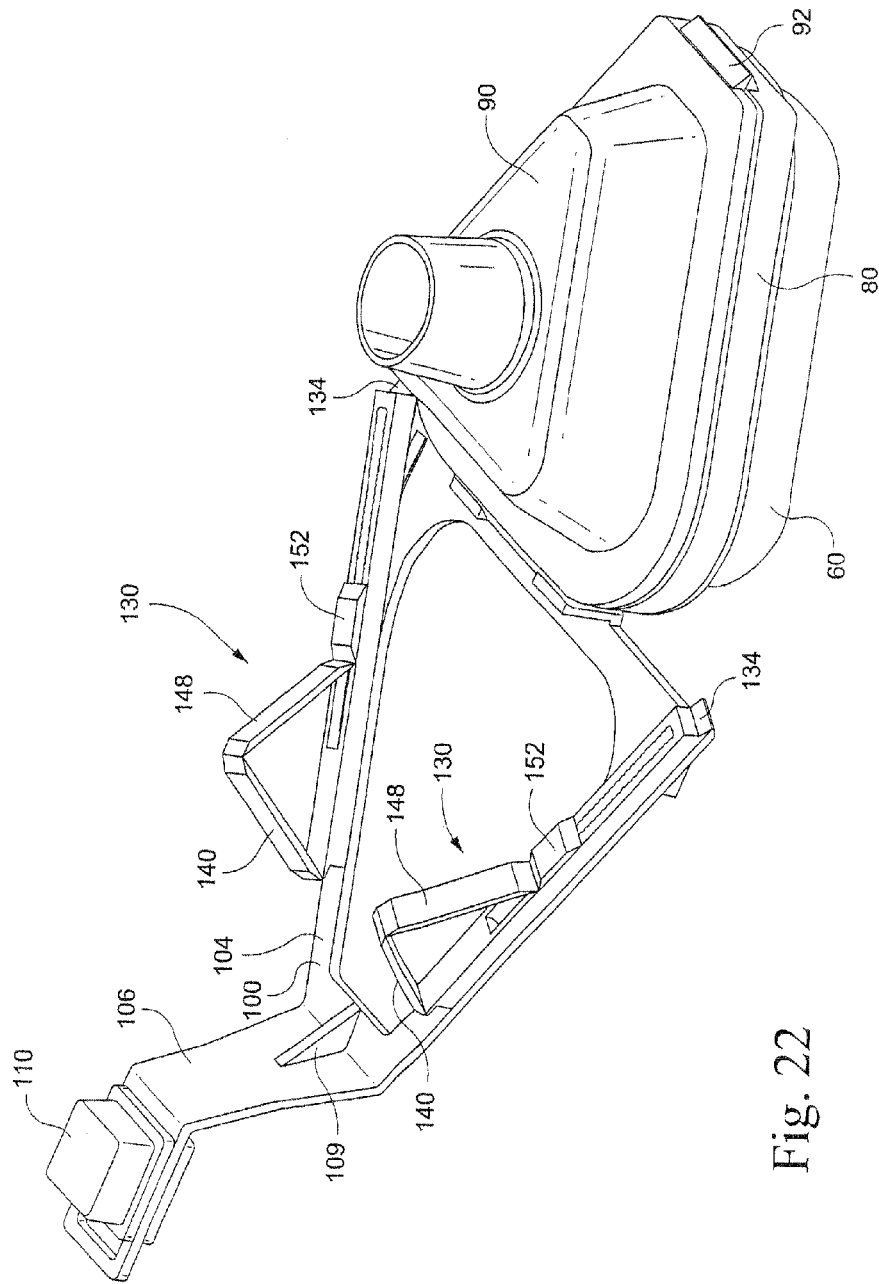
FIG. 22 is a rear perspective view of the embodiment of FIG. 21 with the forehead support adjustment mechanisms folded onto the forehead support portion.
Figure 23:
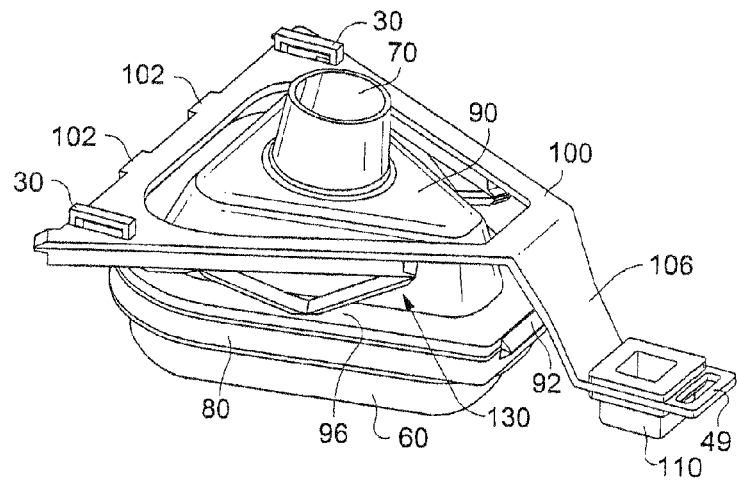
FIG. 23 is a front perspective view of the embodiment of FIG. 17 in a fully assembled state (less straps and air hose)
Figures 24A, 24B:
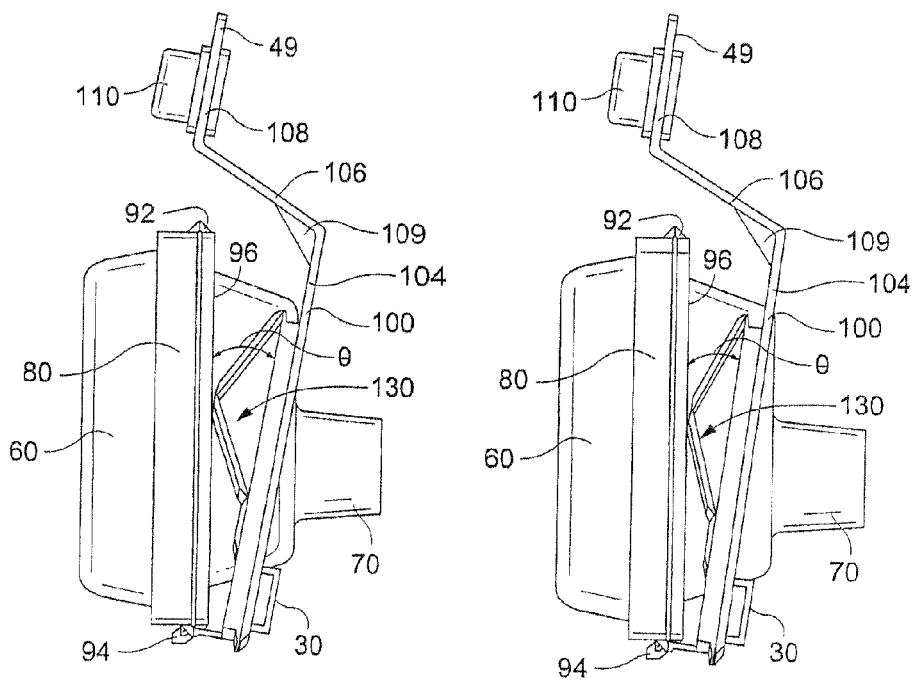
FIGS. 24*a-b* are side elevational views of the embodiment of FIG. 17 showing two different forehead support adjustments.

FIG. 22 is a rear perspective view of the mask of this embodiment where the forehead support adjustment mechanisms 130, through hinges 134, have been folded down onto a rear surface of the forehead support portion 100 of mask frame 20. Forehead support portion 100 can include stabilizing portions 170 (see FIG. 21), such as raised ridges or walls, slots or other structure, to engage the adjustment channel members 132 or other portions of the forehead support adjustment mechanisms 130 to provide lateral and other support to the mechanisms 130 when they are in their final folded position. At this point, the cushion supporting portion 80/air inlet portion 90 folded subassembly can be folded toward the forehead support portion 100 of the mask until subassembly comes into contact with the upstanding portion of the adjustable height members 138, with the adjustable height members 138 positioned on opposing sides of the cushion supporting portion 80/air inlet portion 90 folded subassembly and between the forehead support portion 100 and the cushion supporting portion 80/air inlet portion 90 folded subassembly. See FIGS. 23-24. In the shown embodiment, the adjustable height members 138 are shown as contacting a surface 96 of the air inlet portion 90, although this can be altered as desired so that the adjustable height members 138 contact other portions of the cushion supporting portion 80/air inlet portion 90 folded subassembly.

By altering the lengthwise positions of the adjustment tabs 152 in the adjustment portions 158 of the channels 154, the height of the adjustable height members 138 can be adjusted with respect to the forehead support portion 100, thereby altering an angle θ (at hinge 102) between the forehead support portion 100 and the cushion supporting portion 80/air inlet portion 90 folded subassembly, and thus, altering a corresponding relative height between the forehead pad 110 and the cushion 60. Compare FIGS. 24a and 24b. The height of adjustable height member 138 is higher in FIG. 24a because the adjustment tab 152 is positioned in the adjustment portion 158 of channel 154 nearer hinge 136 in FIG. 24a, thereby resulting in the forehead pad 110 being relatively positioned more toward the front of the mask than in FIG. 24b to better accommodate a user having a more protuberant forehead. For instance, the adjustment shown in FIG. 24a corresponds more with a user as shown in FIG. 5b while the adjustment shown in FIG. 24b corresponds more with a user as shown in FIG. 5c. The user can easily adjust the relative position of the forehead pad 110 through manual adjustment of the height of the adjustable height member 138 by moving the adjustment tab 152 in the channel 154. In this embodiment, the angle of the forehead pad 110 will change with respect to the user within the range of adjustment provided. However, this is accommodated by the resiliency of the forehead pad and can be altered within certain parameters by altering the angle of upright portion 46, and/or a user-contacting portion of the forehead pad 110 with respect to a plane of forehead support portion 100. Alternatively, hinge 102 can be replaced by a double hinge to minimize relative angle changes in the forehead pad 110 as the relative height of the forehead pad is adjusted. Alternatively, the forehead pad can have a cylindrical surface to accommodate varying angles of contact with the forehead.

Strap attachment portions 49 and 30 are provided on the forehead support portion 100 and the cushion supporting portion 80 or air inlet portion 90 for attaching to headgear or straps to secure the mask to the head and facial region of the user. Although the adjustment mechanisms 130 are shown as being attached to the forehead support portion 100, alternative embodiments can be constructed by attaching the adjustment mechanisms to the cushion support portion 80 and/or the air inlet portion 90 and contacting against the forehead support portion 100. Alternatively, the use of a single adjustment mechanism or three or more adjustment mechanisms is contemplated, as well as the use of separately molded adjustment mechanisms.

Figure 25:
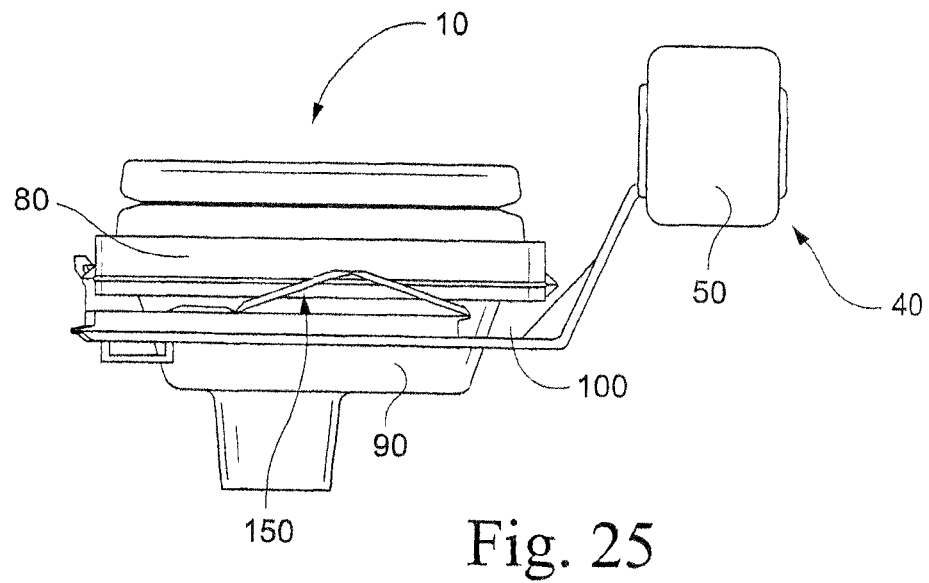
FIG. 25 is a side elevational view of a further embodiment of the present invention incorporating the folding frame design of FIGS. 17-24 and the forehead support of FIGS. 1-16.
Figure 26:
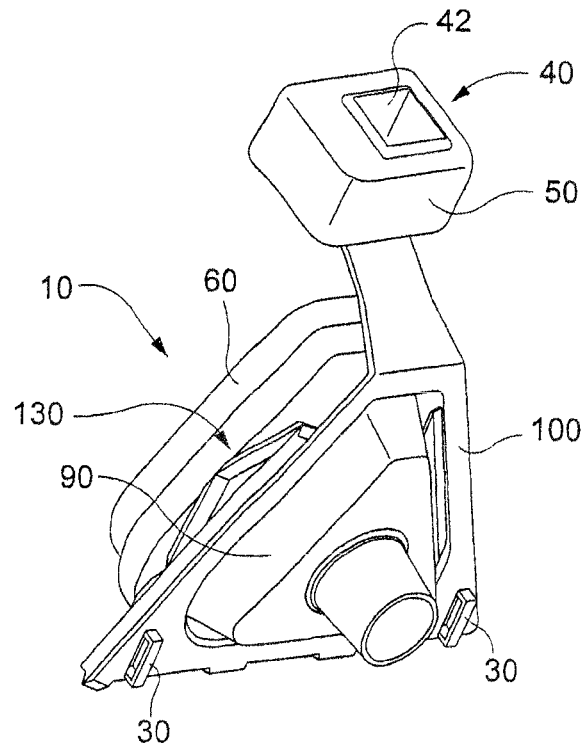
FIG. 26 is a front, top perspective view of the embodiment of FIG. 25.
Figure 27:
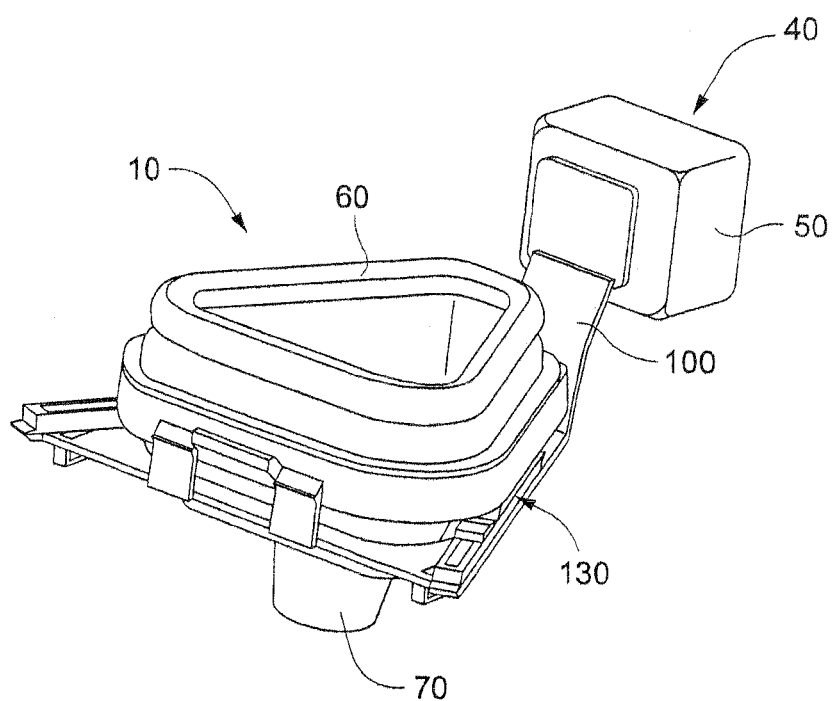
FIG. 27 is a rear, bottom perspective view of the embodiment of FIG. 26.

FIGS. 25-27 show a further embodiment of the present invention incorporating aspects from the mask of FIGS. 17-24 and the forehead support of FIGS. 1-16. In this embodiment, the forehead support portion supports a forehead support member 42 and forehead pad similar to the embodiments shown in FIGS. 1-16. This embodiment also shows use of the mask frame and forehead adjustment mechanisms of the embodiment shown in FIGS. 17-24. Thus, this embodiment gives a wider range of forehead pad adjustability than either of the other two groups of mask embodiments alone. In a modification of this embodiment, the forehead support adjustment mechanisms 130 could be removed or replaced by generally fixed members to combine the one-piece, disposable frame aspects of FIGS. 17-24 with the forehead pad adjustment of FIGS. 1-16.

In order to enable the mask to be molded as one piece, allowance must be made for variation in the desirable characteristics of the different sections of the molding. For example, the mask frame 20 must be rigid, but the mask cushion 60 must be flexible enough to provide comfort and good sealing properties while the forehead support member 42 must be resilient. To make the mask out of one material, such as polypropylene, while providing the differing levels of flexibility desired in the various components, the molding process can provide a changing gradient of material density, as can be achieved by forms of gas assisted injection molding, resulting in a change in rigidity. Another option, which could be used in addition to the changing gradient of material density, is the use of a continuous gradient of material thickness or by stepped contours or introduction of ribbing to provide reinforcement in certain areas where more rigidity is required.

An alternative construction can involve the incorporation of a separate mask cushion 60 to the mask frame 20. The mask cushion 60 can be made of material different to the mask frame 20 or can be made of the same material and may be attached by using any of the methods known in the art, such as friction fit, strapping, clips, or adhesive. Alternatively, the mask cushion 60 can be overmolded onto the mask frame or co-molded with the mask frame 20 in accordance with methods known in the art of molding. In such examples, placement of appropriate channeling in the mask frame 20 allows for bleed-through of cushion molding material so as to achieve enhanced attachment of the mask cushion 60 to the mask frame 20. This can be especially desirable if the mask cushion 60 is made of a material that does not readily form a chemical bond with the material of the mask frame 20. This technique may also be used to provide even softer material between the mask frame 20 and the user at certain contact points, a decorative effect, or visually vivid and tactile labeling. The key polymers capable of incorporating living hinges and which would be suited to this application are polypropylene and styrene-butadiene copolymers such as K-Resin®.

It is intended that various features of the various embodiments described above can be combined to create different embodiments of the nasal mask of the present invention. The embodiments describe above are exemplary only and are not exhaustive of the scope of the invention. It is also intended that changes and modifications can be made to the embodiments described above without departing from the scope of the invention.

What is claimed is:

1. An integrated respiratory mask for delivery of pressurized, breathable gas to a wearer's airways, the integrated respiratory mask comprising:
    a cushion supporting portion having a periphery;
    an air inlet portion joined to the cushion supporting portion by a first integral hinge;
    a forehead support portion joined to the cushion supporting portion by a second integral hinge; and
    a sealing member formed on the periphery of the cushion supporting portion, the sealing member structured to form a pneumatic seal with the air inlet portion when the first integral hinge is folded to engage the air inlet portion with the cushion supporting portion.

2. The integrated respiratory mask of claim 1, wherein the cushion supporting portion, the air inlet portion, and forehead support portion comprise one piece.

3. The integrated respiratory mask of claim 1, wherein the forehead support portion comprises a forehead pad mounting portion, a main body portion, and an offset portion, the offset portion structured to offset the forehead pad mounting portion relative to the main body portion.

4. The integrated respiratory mask of claim 3, wherein a forehead pad is provided to the forehead pad mounting portion.

5. The integrated respiratory mask of claim 4, wherein the forehead pad is adjustable.

6. The integrated respiratory mask of claim 3, wherein the forehead pad mounting portion comprises a strap attachment portion.

7. The integrated respiratory mask of claim 3, wherein the offset portion comprises a rib to strengthen the offset portion.

8. The integrated respiratory mask of claim 1, wherein the air inlet portion comprises a latch located opposite of the first integral hinge and the cushion supporting portion comprises a lip structured to receive the latch when the air inlet portion is folded onto the cushion supporting portion.

9. The integrated respiratory mask of claim 1, further comprising a mask cushion joined to the cushion supporting portion.

10. The integrated respiratory mask of claim 9, further comprising one piece and being formed from a single material.

11. The integrated respiratory mask of claim 10, wherein the mask cushion is less rigid than the remainder of the mask.

12. The integrated respiratory mask of claim 11, wherein the density of the material of the mask cushion is different from the density of the material of the remainder of the mask.

13. The integrated respiratory mask of claim 10, further comprising stepped contours or ribs for increased rigidity.

14. The integrated respiratory mask of claim 9, wherein the mask cushion comprises a different material from the remainder of the mask, such that the mask cushion is less rigid than the remainder of the mask.

15. The integrated respiratory mask of claim 14, wherein the mask cushion is attached to the mask by a mechanical interlock formed by overmolding.

16. The integrated respiratory mask of claim 15, wherein the cushion supporting portion further comprises channels to allow bleed through of the material of the mask cushion during overmolding of the mask cushion.

17. The integrated respiratory mask of claim 1, wherein the forehead support portion further comprises a pair of strap attachment portions.

18. The integrated respiratory mask of claim 1, further comprising a pair of forehead support adjustment mechanisms to adjust the forehead support portion relative to the cushion supporting portion.

19. The integrated respiratory mask of claim 18, wherein the pair of forehead support adjustment mechanisms adjust the angle and/or the distance of the forehead support portion relative to the cushion supporting portion.

20. The integrated respiratory mask of claim 18, wherein the pair of forehead support adjustment mechanisms are joined with the forehead support portion by integral hinges.

* * * * *